(12) United States Patent
Kaufman et al.

(10) Patent No.: US 10,814,108 B2
(45) Date of Patent: Oct. 27, 2020

(54) DRUG-COATED BALLOON

(71) Applicant: Intersect ENT, Inc., Menlo Park, CA (US)

(72) Inventors: Richard E. Kaufman, Los Gatos, CA (US); John Joseph Stankus, San Jose, CA (US); James Su, Newark, CA (US)

(73) Assignee: Intersect ENT, Inc., Menlo Park, CA (US)

( * ) Notice: Subject to any disclaimer, the term of this patent is extended or adjusted under 35 U.S.C. 154(b) by 0 days.

(21) Appl. No.: 16/790,464

(22) Filed: Feb. 13, 2020

(65) Prior Publication Data

US 2020/0179659 A1   Jun. 11, 2020

Related U.S. Application Data

(63) Continuation of application No. 16/523,836, filed on Jul. 26, 2019, now Pat. No. 10,603,473, which is a
(Continued)

(51) Int. Cl.
*A61L 29/16* (2006.01)
*A61M 25/10* (2013.01)
(Continued)

(52) U.S. Cl.
CPC .......... *A61M 25/10* (2013.01); *A61L 29/085* (2013.01); *A61L 29/16* (2013.01); *A61M 29/02* (2013.01);
(Continued)

(58) Field of Classification Search
CPC .......... A61L 31/16; A61L 31/10; A61L 29/16; A61K 9/146; A61K 9/0075; A61K 9/145;
(Continued)

(56) References Cited

U.S. PATENT DOCUMENTS 5,209,732 A   5/1993   Lampropoulos et al.
5,562,619 A   10/1996  Mirarchi et al.
(Continued)

FOREIGN PATENT DOCUMENTS

CN   102458497 A   5/2012
JP   8-317970 A    12/1996
(Continued)

OTHER PUBLICATIONS

Extended European Search Report dated Dec. 5, 2018, for EP Application No. 16 740 876.4, filed on Jan. 22, 2016, 9 pages.
(Continued)

*Primary Examiner* — Manuel A Mendez
(74) *Attorney, Agent, or Firm* — Cooley LLP

(57) ABSTRACT

Described here are devices, systems, and methods for treating conditions or diseases of the nose, ear, or throat with an expandable device having a drug coating. The expandable devices may be delivered to a body cavity in a low-profile configuration and expanded to contact surrounding tissue. The expandable devices may deliver or release the drug coating to the tissue. Multiple expansions of a single device may be employed during treatment. Various coating excipients and manufacturing parameters for the expandable devices may also be adjusted to enhance or slow transfer of the drug coating and/or release of the drug to the target tissue site. The drug transferred to the tissue may act as an in situ depot that enables maintenance of a therapeutic level of locally delivered drug for a desired time period after removal of the expandable devices.

39 Claims, 4 Drawing Sheets

Related U.S. Application Data continuation of application No. 15/004,807, filed on Jan. 22, 2016, now Pat. No. 10,441,757.

(60) Provisional application No. 62/106,692, filed on Jan. 22, 2015.

(51) Int. Cl.
*A61M 29/02* (2006.01)
*A61L 29/08* (2006.01)

(52) U.S. Cl.
CPC .. *A61L 2300/222* (2013.01); *A61M 2025/105* (2013.01); *A61M 2210/065* (2013.01); *A61M 2210/0662* (2013.01); *A61M 2210/0668* (2013.01); *A61M 2210/0675* (2013.01); *A61M 2210/0681* (2013.01); *A61M 2210/105* (2013.01)

(58) Field of Classification Search
CPC ........ A61K 45/06; A61K 9/14; A61K 9/0004; C07D 471/04; C07D 487/04
See application file for complete search history.

(56) References Cited

U.S. PATENT DOCUMENTS

| | | | |
|---|---|---|---|
| 5,702,754 A | 12/1997 | Zhong | |
| 6,329,386 B1 | 12/2001 | Mollison | |
| 6,533,772 B1 | 3/2003 | Sherts et al. | |
| 7,105,013 B2 | 9/2006 | Durcan | |
| 7,559,925 B2 | 7/2009 | Goldfarb et al. | |
| 7,717,933 B2 | 5/2010 | Becker | |
| 7,740,642 B2 | 6/2010 | Becker | |
| 7,753,929 B2 | 7/2010 | Becker | |
| 8,100,933 B2 | 1/2012 | Becker | |
| 8,142,422 B2 | 3/2012 | Makower et al. | |
| 8,414,473 B2 | 4/2013 | Jenkins et al. | |
| 8,905,922 B2 | 12/2014 | Makower et al. | |
| 9,138,569 B2 | 9/2015 | Edgren et al. | |
| 9,381,328 B2 | 7/2016 | Xie et al. | |
| 9,554,817 B2 | 1/2017 | Goldfarb et al. | |
| 9,603,506 B2 | 3/2017 | Goldfarb et al. | |
| 10,166,369 B2 | 1/2019 | Jenkins et al. | |
| 10,441,757 B2 | 10/2019 | Kaufman et al. | |
| 10,603,473 B2 | 3/2020 | Kaufman et al. | |
| 2002/0082584 A1 | 6/2002 | Rosenman et al. | |
| 2007/0250105 A1 | 10/2007 | Ressemann et al. | |
| 2008/0065011 A1 | 3/2008 | Marchand et al. | |
| 2009/0163890 A1 | 6/2009 | Clifford et al. | |
| 2009/0226502 A1* | 9/2009 | Chen | A61L 29/085 424/423 |
| 2010/0198190 A1 | 8/2010 | Michal et al. | |
| 2010/0211007 A1 | 8/2010 | Lesch, Jr. et al. | |
| 2010/0272773 A1 | 10/2010 | Kangas et al. | |
| 2011/0144577 A1 | 6/2011 | Stankus et al. | |
| 2012/0143132 A1 | 6/2012 | Orlowski | |
| 2012/0150142 A1 | 6/2012 | Weber et al. | |
| 2013/0053947 A1 | 2/2013 | Kangas et al. | |
| 2013/0066358 A1 | 3/2013 | Nalluri et al. | |
| 2013/0142834 A1 | 6/2013 | Esfand et al. | |
| 2014/0046255 A1 | 2/2014 | Hakimimehr et al. | |
| 2014/0073911 A1 | 3/2014 | Munrow et al. | |
| 2014/0074140 A1 | 3/2014 | Johnson et al. | |
| 2014/0100445 A1 | 4/2014 | Stenzel et al. | |
| 2014/0200443 A1 | 7/2014 | Chang et al. | |
| 2015/0065810 A1 | 3/2015 | Edgren et al. | |
| 2015/0112134 A1 | 4/2015 | Suehara et al. | |
| 2015/0142046 A1 | 5/2015 | Andersen et al. | |
| 2015/0182732 A1 | 7/2015 | Zeng et al. | |
| 2015/0273117 A1 | 10/2015 | Wang | |
| 2016/0045718 A1 | 2/2016 | Pruitt et al. | |
| 2016/0121088 A1 | 5/2016 | Fox et al. | |
| 2016/0144158 A1 | 5/2016 | Abbate | |
| 2016/0213890 A1 | 7/2016 | Kaufman et al. | |
| 2017/0165064 A1 | 6/2017 | Nyuli et al. | |
| 2019/0160266 A1 | 5/2019 | Ngo-Chu et al. | |
| 2019/0374751 A1 | 12/2019 | Finson et al. | |

FOREIGN PATENT DOCUMENTS

| | | |
|---|---|---|
| JP | 2008-099917 A | 5/2008 |
| JP | 2011-528275 A | 11/2011 |
| JP | 2013-515591 A | 5/2013 |
| JP | 2014-200269 A | 10/2014 |
| WO | WO-2006/107957 A2 | 10/2006 |
| WO | WO-2006/107957 A3 | 10/2006 |
| WO | WO-2010/009335 A1 | 1/2010 |
| WO | WO-2010/121840 A2 | 10/2010 |
| WO | WO-2010/121840 A3 | 10/2010 |
| WO | WO-2010/126912 A1 | 11/2010 |
| WO | WO-2010/132648 A1 | 11/2010 |
| WO | WO-2011/082139 A1 | 7/2011 |
| WO | WO-2013/130464 A1 | 9/2013 |
| WO | WO-2014/066085 A1 | 5/2014 |
| WO | WO-2014/075513 A1 | 5/2014 |
| WO | WO-2016/118923 A1 | 7/2016 |

OTHER PUBLICATIONS

Final Office Action dated Apr. 11, 2019, for U.S. Appl. No. 15/004,807, filed Jan. 22, 2016, 12 pages.
Final Office Action dated Jan. 14, 2020, for U.S. Appl. No. 16/436,363, filed Jun. 10, 2019, 6 pages.
International Search Report dated Mar. 31, 2016, for PCT Application No. PCT/US2016/014622, filed Jan. 22, 2016, 2 pages.
International Search Report dated Aug. 28, 2019, for PCT Application No. PCT/US2019/036506, filed Jun. 11, 2019, 3 pages.
International Search Report dated Apr. 7, 2020, for PCT Application No. PCT/US2020/014090, filed Jan. 17, 2020, 2 pages.
Non-Final Office Action dated Dec. 31, 2018, for U.S. Appl. No. 15/004,807, filed Jan. 22, 2016, 10 pages.
Non-Final Office Action dated Aug. 30, 2019, for U.S. Appl. No. 16/436,363, filed Jun. 10, 2019, 9 pages.
Notice of Allowance dated Jul. 17, 2019, for U.S. Appl. No. 15/004,807, filed Jan. 22, 2016, 7 pages.
Notice of Allowance dated Aug. 13, 2019, for U.S. Appl. No. 15/004,807, filed Jan. 22, 2016, 6 pages.
Notice of Allowance dated Nov. 22, 2019, for U.S. Appl. No. 16/523,836, filed Jul. 26, 2019, 7 pages.
Notice of Allowance dated Feb. 27, 2020, for U.S. Appl. No. 16/436,363, filed Jun. 10, 2019, 5 pages.
St. Croix, B. et al. (2000). "Genes expressed in human tumor endothelium," *Science* 289:1197-1202.
Written Opinion of the International Searching Authority dated Mar. 31, 2016, for PCT Application No. PCT/US2016/014622, filed Jan. 22, 2016, 7 pages.
Written Opinion of the International Searching Authority dated Aug. 28, 2019, for PCT Application No. PCT/US2019/036506, filed Jun. 11, 2019, 12 pages.
Written Opinion of the International Searching Authority dated Apr. 7, 2020, for PCT Application No. PCT/US2020/014090, filed Jan. 17, 2020, 8 pages.

* cited by examiner

DRUG-COATED BALLOON

CROSS-REFERENCE TO RELATED APPLICATIONS

This application is a continuation of U.S. application Ser. No. 16/523,836, filed on Jul. 26, 2019, now issued as U.S. Pat. No. 10,603,473, which is a continuation of U.S. application Ser. No. 15/004,807, filed on Jan. 22, 2016, now issued as U.S. Pat. No. 10,441,757, which claims priority to U.S. Provisional Application Ser. No. 62/106,692, filed on Jan. 22, 2015, each of which is hereby incorporated by reference in its entirety.

FIELD

This application is generally related to expandable devices for treating conditions or diseases associated with bodily structures of the nose, ear, and throat, devices for delivering the expandable devices, and methods of using them.

BACKGROUND

Rhinosinusitis is a common paranasal sinus condition that is generally understood as encompassing sinusitis and/or rhinitis. Typically, rhinosinusitis is characterized by major symptoms such as nasal discharge, nasal obstruction, facial congestion, facial pain/pressure, loss of smell, and fever, and minor symptoms such as headache, ear pain/pressure, halitosis, dental pain, cough, and fatigue.

Allergic rhinitis is associated with a group of symptoms affecting the nose that occurs when an individual with the condition breaths in an allergen, such as dust, mold, or animal dander. Allergens cause the release of histamine, which usually causes sneezing, itchy and watery eyes, runny nose, swelling and inflammation of the nasal passages, an increase in mucus production, and for some individuals, hives or other rashes. Allergic rhinitis due to pollen is commonly known as hay fever.

Current treatments for these and other nasal conditions, as well as certain otic and throat conditions, are primarily pharmaceutical. Drugs in pill form are widely available and easy to take, but can have several drawbacks. An orally administered drug may require considerable time to work through the body to become effective, and may have negative side effects that can impact the daily life of the patient. Also, the drug may need to be taken frequently for continued symptom relief. Nasal, otic, and throat topical drug delivery represents an attractive alternative approach for the treatment of local nasal, otic, and throat diseases. However, current technologies for local drug delivery of drugs in either liquid or powder form, and by spray or direct application, can be limited by poor patient compliance when repeated doses are required, or poor efficacy due to challenges in delivering a drug to more distal sinus and ear anatomies.

Another challenge with topical drug delivery is presented when the nasal condition involves treatment of mucosal tissue. Most mucosal epithelial tissues are covered with a glycoprotein rich mucus layer. This mucus layer is a dynamic layer that generally works to clear contaminants from the respiratory system. It typically has a transit and turnover time of approximately 15-20 minutes. A locally delivered drug must pass through this mucus layer and be taken up by the mucosal epithelium before it is moved away from the target tissue site.

Accordingly, for certain nasal, otic, and throat conditions, it may be desirable to treat distal anatomies by distributing high concentrations of drugs with reduced dosing frequency evenly across treated sites and in the absence of a permanent implant for applications where mechanical support is not necessary. Regarding nasal conditions, it may be useful to have treatments that can both deliver drugs and dilate target sites such as the paranasal sinuses and/or deliver drugs to multiple sites with a single device. When mucosal tissues are affected, it would be desirable to have topical treatments where drugs can be delivered and taken up by tissue before they are cleared from the site by mucociliary flow.

BRIEF SUMMARY

Described herein are expandable devices coated with a therapeutic agent (drug) that may be physically transferred to the tissue site of interest upon expansion. After therapeutic agent transfer, the expandable device may be collapsed and removed. The drug coating may be formulated to be transferred with a single expansion, or when multiple expansions with a single device are performed, partially transferred with each expansion. The drug coating transferred to the tissue may act as an in situ sustained release depot that enables maintenance of a therapeutic level of locally delivered drug for a desired time frame (e.g., days, weeks, or months). Some variations of the drug coating are formulated for rapid delivery through the mucous layer of tissue. For example, these formulations may include one or more mucolytic, mucoadhesive, or penetration enhancing agents to hasten drug delivery. In other variations, the expandable device may be combined with an implantable device, such as a stent or scaffold.

Described herein is a method of treating a nasal, otic, or throat condition that may comprise providing an expandable device comprising a drug coating on an external surface thereof and having a low-profile configuration and an expanded configuration, delivering the expandable device in the low-profile configuration to a target tissue site, expanding the expandable device to the expanded configuration, contacting the tissue treatment site with the expanded expandable device for a period of time effective to transfer the drug coating from the external surface to the target tissue site, removing the expandable member from the target tissue site, and maintaining a therapeutic level of locally delivered drug at the target tissue site from the transferred drug coating for a time period effective to treat the target tissue site. The expandable device is typically collapsed prior to its removal from the target tissue site.

Some variations of the method include transferring substantially all the drug coating from the expandable device to the target tissue site with a single expansion. In other variations, the method includes using a single expandable device to treat multiple target tissue sites. For example, a single expandable device could be used to treat multiple sinuses in a patient. Here the drug coating may be formulated so that only a portion of the coating is transferred with each expansion. The drug coating may also be configured, e.g., as multiple layers, to transfer one or more drugs over multiple expansions. Various surface treatments, e.g., plasma treatment or a hydrophilic primer layer, can also be applied to the expandable device to manipulate coating transfer rates.

The expandable devices may be used to treat inflammation of mucosal tissue, e.g., mucociliary tissue, which is present in the nasal passages and sinuses, among other structures of the respiratory system. In some variations, the condition to be treated may be a nasal condition selected from the group consisting of post-surgical inflammation, rhinosinusitis, and rhinitis, including allergic rhinitis. In such variations, the target tissue site may be a paranasal sinus, a sinus ostium, an inferior turbinate, a middle turbinate, a superior turbinate, a nasal cavity, the osteomeatal complex, the nasopharynx, adenoid tissue, or a combination thereof. In other variations, the condition to be treated may be an otic condition selected from the group consisting of post-surgical inflammation, otitis media, Meniere's disease, Eustachian tube dysfunction, and tinnitus. In such variations, the target tissue site may be the Eustachian tube, external ear canal, or inner ear. In other variations, the condition to be treated may be a throat condition selected from the group consisting of post-surgical pain, esophageal cancer, airway stenosis, e.g., tracheal stenosis or subglottic stenosis, chronic laryngitis, tonsillitis, and epiglottitis. The expandable device may also be employed in methods where it may beneficial to both dilate and deliver drugs to the target tissue site.

The expandable device may be compliant, semi-compliant, or non-compliant. Compliant devices may distend upon inflation to the expanded configuration. The expandable devices may be folded, pleated, or wrapped to achieve a low-profile configuration.

In some variations, the expandable device may be an inflatable balloon. In such variations, the inflatable balloon may have an inflation pressure between about 2 atm and 16 atm. Alternatively, the inflation pressure may be between about 4 atm and 6 atm. In other instances, e.g., when the inflatable balloon is non-compliant, the inflation pressure may be at least about 20 atm.

In some variations, the drug coating may comprise a lipophilic drug. In other variations, the drug coating may comprise a corticosteroid. When the expandable device is used to treat nasal conditions, it may be beneficial for the drug coating to comprise mometasone furoate.

In some variations, the period of time effective to transfer the drug coating may be from about 5 seconds to about 2 hours. In other variations, the period of time effective to transfer the drug coating may be from about 10 minutes to about 30 minutes. In yet further variations, the period of time effective to transfer the drug coating may be from about 30 seconds to about 5 minutes. When multiple sinuses are to be treated, it may be beneficial for the drug coating to be transferred with a 5 second expansion, e.g., a 5 second balloon inflation.

In some variations, the time period effective to treat the target tissue site may be between 5 days and 90 days. In other variations, the time period effective to treat the target tissue site may be from about 2 months to about 3 months. For example, the duration of the treatment period may range from about 7 to about 14 days post balloon dilation only, about 7 days to about 21 days post balloon dilation only, and about 28 days post functional endoscopic sinus surgery (FESS) or hybrid treatment.

The drug coating may comprise a drug and an excipient. Multiple drugs and excipients can be included in the drug coating if desired. In some variations, the drug coating may comprise a drug to excipient ratio ranging from about 3:1 to 1:3. For example, the drug to excipient ratio may be 3:1, 3:2, 1:1, 1:2, or 1:3. For nasal conditions, it may be useful to include a corticosteroid, e.g., mometasone furoate, as the drug in the drug coating, as previously stated.

With respect to excipients, the drug coating may comprise at least one of a poly(ethylene glycol); poly(vinyl pyrrolidone); phospholipids; fatty acids; sodium dodecyl sulfate; polysorbates; pluronics; cyclodextrins such as hydroxypropyl-beta-cyclodextrin; sucrose fatty acid monoester; alkyl glycosides such as decyl maltoside and octyl maltoside; oleic acid; sorbitan trioleate; sorbital; mannitol; pectin; trehalose; tributyl citrate; triethyl citrate; glycerol monooleate; thymol; and shellac. In other variations, the drug coating may comprise at least one of a low molecular weight poly(ethylene glycol), glycerol, fatty acids, sebacates, fatty alcohols, lipids, lecithin, oils such as vegetable oils, glycol esters, and propylene glycol. In other variations, the drug coating may comprise at least one of a chitosan, collagen, elastin, silk, silk-elastin, alginate, cellulose, cellulosics such as hydroxypropyl cellulose, hydroxypropyl methylcellulose, methylcellulose, ethylcellulose, dextran, polyalkoanates, hyaluronic acid, gelatin, gellan, carrageenan, polylactide, poly(lactide-co-glycolide), poly(L-lactide-co-ca prolactone), polyglycolide, polyhydroxybutyrate, polyhydroxyvalerate, poly(ethylene glycol), polydioxanone, polyglactin, poly(E-caprolactone), polyglyconate, poly(glycolide-co-trimethylene carbonate), poly(sebacic acid), poly(ester urethane), poly(ester urethane) urea, cross-linked poly(ethylene glycol) (PEG), polyNIPAAM, PEG-poly(lactic acid) (PEG-PLA) block copolymers, and poloxamers.

During manufacturing, the expandable device, e.g., a balloon, may be coated with a drug coating formulation by methods such as spray coating, pipette or syringe coating, or dip coating. Spray coating may achieve improved tissue uptake and drug delivery uniformity. For improved coating adhesion, the expandable device may be cleaned with a solvent and dried prior to coating. In addition, plasma treatment with an inert gas, such as argon or oxygen, after cleaning may increase the cleaning and wettability of the expandable device surface leading to increased coating adhesion and release of the coating upon contact with mucus at the mucosal tissue site. In some variations, the manufacturing method may include cleaning the balloon surface and/or treating the balloon with plasma, inflating the balloon, spray coating the balloon with a drug coating formulation, drying the balloon coating at room temperature or elevated temperature, and re-folding the balloon. In other variations, the manufacturing method may include cleaning the balloon surface and/or treating the balloon with plasma, inflating the balloon, spray coating the balloon with a drug coating formulation, exposing the coated balloon to a solvent vapor (solvent vapor annealing), and re-folding the balloon.

Varying the environmental conditions during the drug coating process may affect the rate of drug release from the expandable device. Certain conditions may favor crystal or amorphous forms of the drug, which in turn can modify the rate of drug release. In some variations, the drug coating is exposed to a solvent vapor after application to modify the drug form in the coating, e.g., to produce more crystalline drug, which is generally associated with longer release rates. Accordingly, by manipulating various conditions, drug release can be tailored to the particular indication and/or anatomy being treated.

DETAILED DESCRIPTION

Figure 1A:
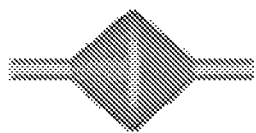
FIGS. 1A-1L depict exemplary shapes for the expandable device.
Figure 1B:
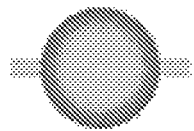
Figure 1C:
Figure 1D:
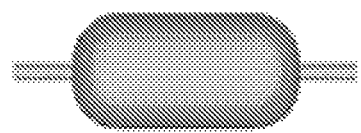

Described here are devices, systems, and methods for treating one or more conditions with an expandable device. Generally, the systems may comprise an expandable device sized and configured for placement in one or more body cavities. The expandable device may be delivered in a low-profile configuration, and may be expanded in the cavity to contact a large surface area of surrounding tissue. The expandable device may be configured to deliver or release one or more drugs to the surrounding tissue and then be removed. The device may be expanded once or multiple times at the same or different treatment sites. Generally, the treatment method may provide therapeutic levels of drug for a desired time period after expansion and removal of the expandable device. The methods and devices may be useful when drug delivery to tissue sites having a mucociliary layer, e.g., the paranasal sinuses, is desired.

The expandable device may have several applications. It may be adapted in size, configuration, and material for different uses, such as in the nose, ear, and throat. The expandable device may be useful in treating conditions involving mucosal inflammation. In some variations, the devices, systems, and methods may be used for treating one or more sinus or nasal conditions including, but not limited to rhinitis, allergic rhinitis, acute sinusitis, and chronic sinusitis. In other variations, the systems, and methods may be implemented during a dilation procedure. For example, one or more drugs (e.g., a corticosteroid) may be delivered to reduce inflammation post ballooning, post dilation, or other surgery of the sinuses and/or sinus ostia. In other variations, one or more drugs may be delivered to the sinus and/or sinus ostia for allergy symptom relief. As another example, an expandable device, such as an inflatable balloon, may be used to deliver drugs to the inferior turbinate for the treatment of allergic rhinitis. Use of a temporary inflatable balloon for drug delivery may in some cases be advantageous over an implant in the inferior turbinate, since the latter may cause a sneezing reflex. As yet another example, it may be used for delivery of an anti-inflammatory (e.g., a corticosteroid) for reduction of inflammation post functional ethmoid surgery, including when mechanical support and a permanent implant may not be necessary.

In other variations, the devices, systems, and methods described here may also be for treating one or more conditions of the ear. For example, an expandable device may deliver drugs to the Eustachian tube post ballooning to treat Eustachian tube dysfunction, which may contribute to otitis media or other diseases of the ear. As another example, the expandable device may be used for drug delivery to the external ear canal for acute otitis media, chronic otitis media or swimmer's ear. It may also be used for drug delivery to the middle and/or inner ear for otitis media, Meniere's disease, tinnitus, or other applicable diseases.

In other variations, the expandable device may also have applications in the throat, where drug delivery may be for post-surgical pain, such as tonsillectomy pain, or for esophageal cancer, airway stenosis (e.g., tracheal stenosis or subglottic stenosis), chronic laryngitis, epiglottitis, other inflammatory diseases, and/or other diseases of the throat.

Also described here are systems and methods for delivering and manufacturing the expandable devices described herein. In some variations, the systems may comprise a delivery device for delivering the expandable device into the body.

Devices

Expandable Devices

The expandable devices described herein may generally be movable between a low-profile configuration and an expanded configuration. The expandable devices may comprise a flexible membrane that may be configured to provide even and consistent contact with, and substantial coverage of, the surrounding tissue upon expansion. In some variations, the flexible membrane may comprise a tubular sheath that may be expanded using a mechanical system coupled to the internal surface of the tubular sheath. In other variations, the flexible membrane may comprise an inflatable structure that may be expanded using a fluid. For example, the inflatable structure may be a balloon, wherein the balloon may be expanded to an expanded configuration by delivery of a liquid (e.g., saline) or gas (e.g., air) to the interior of the balloon. In some variations, the expandable devices may comprise a hub connecting the membrane to a shaft.

The low-profile configuration may be the expandable device in its collapsed state (or non-inflated state), or the expandable device pleated, folded, or wrapped upon itself. In some instances, the low-profile configuration may be the expandable device in a partially collapsed (or partially inflated) state. A sheath or other covering may be used to cover the expandable device. In one variation, a sheath or cover may constrain the expandable device in its low-profile configuration. In this variation, the expandable device may be self-expanding. In some variations, expansion to the expanded configuration is accomplished via inflation with a fluid or a gas.

The expandable device may be non-compliant, semi-compliant, or compliant. While the following description relating to compliance is primarily directed to a balloon, it may apply to expandable devices of other forms and configurations. Balloon compliance is a term generally used to describe the degree to which the diameter of a balloon changes as a function of inflation pressure.

In some variations, the expandable device comprises a compliant balloon. Compliant balloons may be made from materials having low (e.g., Shore A) durometer such as polyurethane, polyvinyl chloride (PVC), polyolefins, and other elastomers, and may be capable of increasing their diameter by about 100% to about 600% as inflation volume of the balloon increases. Compliant balloons typically have an inflation pressure less than about 16 atm. The compliant balloons may have any suitable shape, e.g., as shown in FIGS. 1A-1L. In some variations, compliant balloon shapes may include spherical type shapes that may be useful when drug delivery without mechanical dilation is needed. It is understood that the compliant balloons may be configured to have other shapes and geometries.

Variations of the compliant balloon may generally be low pressure, elastic, and capable of distending significantly (e.g., up to 600%). In some applications, the compliant balloon may be configured to conform to the body cavity in which it is expanded in order to contact a large surface area of the surrounding tissue. The pressure exerted by the compliant balloon when expanded may be sufficient to maintain contact with the tissue, but may not cause unwanted damage (e.g., breaking bone, tissue damage) or reshaping (e.g., displacing tissue). To achieve this, the compliant balloon material may comprise, for example, latex, silicone, polyurethane (PE), polyvinyl chloride (PVC), and/or low durometer Pebax® polyether block amides. Further, the inflation pressure of the compliant balloon may be, for example, between about 2 atm and 16 atm, between about 2 atm and 10 atm, or between about 4 atm and 6 atm. Compliant balloons may be able to conform to irregular geometries in body cavities in order to effectively deliver drugs, for example, in the nasal or sinus cavities, or sinus ostia. For example, a compliant balloon may be used to contact the inferior turbinate for the treatment of allergies. In some variations, the compliant balloons may be molded from suitable materials, e.g., the materials described above. To achieve a low profile delivery configuration, the compliant balloons may be pleated, folded, or wrapped upon themselves.

Alternatively, the expandable device may comprise a non-compliant balloon. Non-compliant balloons may be made from non-elastic materials having higher durometer such as polyethylene terephthalate (PET), crosslinked polyethylene, and nylon polymers. Non-compliant balloons may have an inflation pressure between 10 atm and 22 atm, between 14 atm and 20 atm, or 20 atm or higher, and may only distend by about 5% to about 7%, or about 5% to about 10%, when inflated. The non-compliant balloons may have any suitable shape, e.g., as shown in FIGS. 1A-1L. In some variations, non-compliant balloon shapes may include cylindrical type shapes. It is understood that the non-compliant balloons may be configured to have other shapes and geometries.

The non-compliant balloon may be molded to a desired inflated geometry from non-compliant materials that retain their predetermined size and shape under pressure. To achieve a low profile delivery configuration, the non-compliant balloon may be pleated, folded, or wrapped upon itself. Upon inflation, the balloon may unfurl to expand to the predetermined expanded configuration. The expanded non-compliant balloon may contact a large surface of the surrounding tissue without dilating or damaging the tissue.

In a further variation, the expandable device may comprise a semi-compliant balloon. Semi-compliant balloons are generally formed by compliant materials but have a higher inflation pressure than compliant balloons. For example, semi-compliant balloons may be made from polyethylene terephthalate (PET), nylon polymers, or Pebax® polyether block amides (single or dual layer) but have an inflation pressure of 10 atm to 20 atm. Such balloons may be capable of distending about 18% to about 30% upon inflation. Other semi-compliant balloons may allow for about 5% to about 10% distension, and may have an inflation pressure between about 8 atm to 15 atm, more specifically between about 10 atm to 12 atm. Semi-compliant balloons may both distend with inflation and unfurl with inflation. Semi-compliant and non-compliant balloons may be useful when enlargement or dilation of tissue sites, e.g., sinus ostia, is needed.

Semi-compliant balloons may have any suitable shape, e.g., as shown in FIGS. 1A-1L. It is understood that the semi-compliant balloons may be configured to have other shapes and geometries. In some variations, the semi-compliant balloons may be molded from suitable materials, e.g., the materials described above. To achieve a low profile delivery configuration, the semi-compliant balloons may be pleated, folded, or wrapped upon themselves.

Balloon sizes and shapes may be designed for specific anatomies and applications. While compliant balloons may conform to the particular geometries of a cavity, the balloon may additionally or alternatively be molded to match the general size and shape of the space. For example, cylindrical compliant balloons having sizes of, for example, 3 mm diameter×20 mm length, may be utilized for Eustachian tube treatment (i.e., to treat the cartilaginous portion of the tube). Spherical non-compliant balloons having a diameter of, for example, about 15 mm to about 50 mm, may be used for treatment of the inferior turbinate. When treatment of the sinus ostium is desired, balloons having a diameter of about 4 mm to about 6 mm, and a length or about 10 mm to about 25 mm, may be employed. Shorter lengths may be utilized for pediatric patients. Molding the size and shape of a non-compliant balloon may require more tailoring to the deployment location (i.e., cavity) so that the balloon may amply contact the surrounding tissue upon inflation (without the ability to conform to the tissue) without dilatation. In some variations, the balloons may comprise a multi-lobe shape, where the lobes may have the same or different shapes.

Figure 1E:
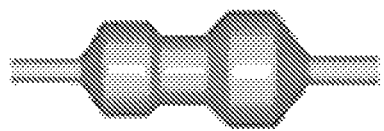
Figure 1F:
Figure 1G:
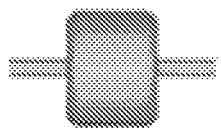
Figure 1J:
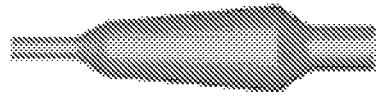
Figure 1H:
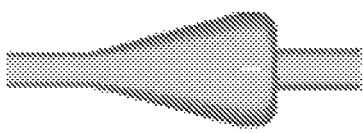
Figure 1K:
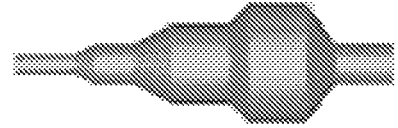
Figure 1I:
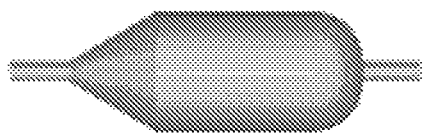
Figure 1L:

Referring to FIGS. 1A-1L, the compliant, non-compliant, and semi-compliant balloons may be conical (FIG. 1A), tapered (FIG. 1J), spherical (FIG. 1B), square (FIG. 1G), a square with a conical end (FIG. 1H), an elongated square with a conical end (FIG. 1C), an elongated sphere (FIG. 1D), an elongated sphere with a conical end (FIG. 1I), or dogbone shaped (FIG. 1E). Alternatively, the balloons may comprise a step or multiple steps of varying height (FIG. 1K), or may be configured to expand in a particular direction (FIGS. 1F and 1L). Directionally expanding balloons may be useful e.g., when it is desired to deliver drug to the inferior turbinate but not the nasal septum. Another useful balloon shape may be similar to a star.

Additionally, the balloons may include one or more ports configured for suction, irrigation, deployment of viewing elements (e.g., optic viewers, magnetic imagers, etc.), and/or use with an endoscope or rhinoscope. The balloons may be delivered over a guidewire, with fiberoptic guidance, or via a conformable shaft. In some variations, the balloons may be configured to be delivered by a physician using a single hand. To achieve a low-profile delivery configuration, the compliant, non-compliant, and semi-compliant balloons may be pleated, folded, or wrapped upon themselves.

Drug Coating

In some variations, the expandable device may be configured to release one or more drugs therefrom. The drug may be part of a coating on the outer surface of the expandable device. In addition to the drug, the coating may also include an excipient or combination of excipients. Suitable excipients include without limitation, poly(vinyl pyrrolidone), polysorbates, poly(ethylene glycol), propylene glycol, glycerol caproate, and combinations and mixtures thereof.

The drug coating may cover the entire expandable device or a portion thereof. For example, the drug coating may be patterned on the expandable device or provided on specific areas of the expandable device, depending on, e.g., the anatomy to be treated. For example, the pattern could include solid or dashed lines of the drug coating, the drug coating dotted on the expandable device, or the drug coating provided as a spiral around the expandable device, etc. The thickness of the drug coating may range from about 10 μm to about 500 μm. In some variations, the thickness of the drug coating can be varied, e.g., structured to be thicker on some areas of the expandable device than others. The drug coating may be formulated to have a similar compliance as the expandable device, with an appropriate ductility to prevent breaking and flaking upon distension or unfolding of the expandable device. In addition to the drug, the coating formulation may include other compounds or additives, such as excipients, binding agents, plasticizers, solvents, surfactants, chelators, penetration enhancers, mucoadhesives, mucolytics, and the like. When the site to be treated includes mucosal or mucociliary tissue, it may be useful for the drug coating to include excipients such as a penetration enhancer, a mucoadhesive and/or a mucolytic to enhance drug delivery across the mucus layer. In some variations, excipients having a molecular weight of 1000 or less may be beneficial in enhancing drug uptake through mucosal tissue.

Another coating (e.g., a topcoat) may be applied on the drug coating to protect it prior to deployment of the expandable device or to facilitate release of the drug (e.g., by priming the surface of the expandable device with a hydrophilic priming agent, or by including a hydrophilic priming agent in the topcoat). The topcoat may lack an active agent, but in some instances it may include small amounts of one or more active agents. In some variations, the topcoat is configured to dissolve or degrade upon contact with the target tissue site but before the expandable device is expanded.

The coating formulation may comprise an excipient to plasticize the coating and/or enhance film integrity. An optional plasticizer may be added to increase ductility and integrity of the coating. Examples of plasticizers may include low molecular weight poly(ethylene glycol), glycerol, polysorbates, fatty acids, sebacates, fatty alcohols, lipids, lecithin, oils such as vegetable oils, glycol esters, propylene glycol, and castor oil.

An excipient or polymer may be added to the coating formulation to enhance film forming and coating integrity. These materials may be natural or synthetic. Natural polymers may include chitosan, collagen, elastin, silk, silk-elastin, alginate, cellulose, dextran, polyalkoanates, hyaluronic acid, gelatin, and gellan. Synthetic bioresorbable polymers may include polylactide (PLA), poly(lactide-co-glycolide), poly(L-lactide-co-ε-ca-prolactone), polyglycolide, polyhydroxybutyrate, polyhydroxyvalerate, poly (ethylene glycol) (PEG), polydioxanone, polyglactin, poly (ε-caprolactone), polyglyconate, poly(glycolide-co-trimethylene carbonate), poly(sebacic acid), poly(ester urethane) and poly(ester urethane) urea.

When PEG is used, its molecular weight may be adjusted to improve coating properties. In general, the molecular weight of PEG ranges from about 5 kDa to about 10 kDa. In some variations, low molecular weight PEG (e.g., less than about 1.2 kDa) may enhance the rate of drug release and mucosal tissue uptake. In other variations, high molecular weight PEG (e.g., more than about 1.2 kDa) may slow the drug release rate over multiple inflations or delay mucosal tissue uptake. Alternatively, the coating can include layers of PEG having different molecular weights. For example, layers could alternately include high and low molecular weight PEG when multiple inflations are being contemplated.

Cross-linked versions of synthetic coating excipients may also be used and include without limitation, crosslinked PEG, polyNIPAAM, PEG-PLA block copolymers, and thermally cross-linked polaxamers (e.g., Pluronics). Crosslinked PEGs may consist of pre-reacted reactive PEGs such as mixtures of reactive multi-arm PEG succinimydyl succinate and multi-arm PEG amine. Either 4-arm PEG or 8-arm PEG may be utilized to control the crosslink density and swell ratio. Other multi-arm PEG-NETS (N-hydroxylsuccinimide) esters such as PEG succinimidyl glutarate may be used. Cellulosics may also be added to the coating formulation.

The formulation may also comprise an excipient for enhancing or slowing coating transfer, enhancing or slowing drug release from the coating, and/or enhancing adhesion to tissue. Particular combinations of excipients and drugs may help to allow the coating to be released from the outer membrane of the expandable device and to adhere to mucus and/or mucosal tissue. Excipients having mucoadhesive properties may be useful and include without limitation, chitosan, polyacrylic acid, polyglutamic acid, carboxymethylcellulose, sodium hyaluronate, and sodium alginate. In some variations, the coating is formulated to be hydrophobic to prevent washout during procedures where tissue sites undergo irrigation.

Specifically, in some instances, it may be desirable for the drug to excipient ratio to be high to enhance fast release of drug from the expandable device during a short time period of inflation. Examples include drug to excipient ratios of 1:3 or higher, or 1:1 or higher. In some instances, moisture and/or mucous from the body cavity after delivery may soften the coating and help to allow the coating to be transferred to tissue. In other instances, the excipient may be amphiphilic (i.e., possess both hydrophilic and lipophilic properties) to promote hydrophilic release from the expandable device when moist and lipophilic interaction with the drug. Examples of amphiphilic polymers and excipients may include poly(ethylene glycol), poly(vinyl pyrrolidone), phospholipids, fatty acids, sodium dodecyl sulfate, polysorbates, poloxamers, hydroxypropyl-beta-cyclodextrin, and sucrose fatty acid monoester.

Alternatively, the drug to excipient ratio may be adjusted to retard or slow the release of drug to a tissue site. Here higher lipophilic drug to hydrophilic excipient ratios, e.g., ratios of 1:1, 2:1, or 3:1, may be used to slow dissolution of the drug, and thus slow release. These ratios may be useful when a single device will be used to treat multiple sites and/or undergo multiple expansions.

Additionally or alternatively, the drug itself may be lipophilic. In these variations, if the expanded expandable device presses against and conforms to the tissue at the treatment site, the lipophilic nature of the drug(s) contained in the coating on the outside surface of the expandable device may promote transfer to and absorption by the tissue. Moisture within the body cavity (e.g., the sinus, Eustachian tube and other applicable bodily structures described herein) may facilitate this transfer. Other factors that may affect drug transfer from the expandable device (e.g., the balloon) include the amount of contact pressure exerted by the expandable device, the amount of contact of the expandable device to the tissue site, and the amount of injury to the surface of the tissue site. The physician may also irrigate the tissue and/or expandable device prior to device deployment to enhance drug release from the device.

Once the coating is transferred to tissue, e.g., mucosal tissue, within a body cavity, it may act as an in situ depot that enables maintenance of a therapeutic local level of drug for a desired time frame. In some instances, the coating containing the one or more drugs may be at least partially biodegradable and/or biosoluble. As the drug and/or coating degrades and/or dissolves over the course of the desired time frame, the drugs may be released to the target tissue and to the anatomies distal to the target tissue. In some variations, the use of cross-linked coating excipients may help maintain the drug at the target tissue site for the desired time frame. In other variations, the inclusion of high molecular weight excipients in the coating may enhance residence time of the drug at the target tissue site. In yet further variations, incorporating the crystal form of the drug in the coating may help to increase the efficiency of drug delivery at the target tissue site.

In some instances, use of a non-compliant or semi-compliant balloon (versus a compliant balloon) may increase the efficiency of drug uptake at a mucosal tissue site. This is because the higher pressures required to inflate the balloons may displace the mucous layer and also lead to epithelial tissue injury, which in turn may enhance drug delivery into the tissue. Tissue injury may also be induced by employing a balloon having spikes or a rough surface molded or adhered thereto, or a balloon capable of scoring, cutting, and/or tearing tissue.

In other instances, use of a mucoadhesive excipient may increase the efficiency of drug delivery at the tissue site. Exemplary mucoadhesive excipients include without limitation, carbomers, glyceryl monooleate, hypromellose, oleic acid, polycarbophil, polyethylene oxide, poly(ethylene glycol), and sodium alginate. Other mucoadhesives could obtain their adhesive properties by wetting of a soluble coating or polymer, charge adhesion (e.g., of anionic polymers such as polyacrylic acid, cellulosics, chitosan, gellan, carbopol, etc.), and covalent adhesion with e.g., a protein reactive gel such as PEG-NETS. In one variation, the mucoadhesive is poly(ethylene glycol).

Penetration enhancers may also be included in the coating formulation to enhance drug delivery through, e.g., the mucous layer, and to the tissue site. Exemplary penetration enhancers include, but are not limited to, dimethyl sulfoxide, glyceryl monooleate, glycofurol, isopropyl myristate, isopropyl palmitate, lanolin, light mineral oil, linoleic acid, menthol, myristic acid, myristyl alcohol, oleic acid, oleyl alcohol, palmitic acid, polyoxyethylene alkyl ethers, polyoxylglycerides, pyrrolidone, sodium lauryl sulfate, thymol, tricaprylin, triolein, and combinations and mixtures thereof.

The expandable device may comprise any suitable drug or agent, depending on the desired use of the device. The drug or agent may comprise at least one of a diagnostic agent or a therapeutic agent, for example. Suitable classes of drugs include, for example, local anesthetics, painkillers, vasoconstrictors, antiseptics, antioxidants, anti-inflammatory agents, anti-allergens, anti-cholinergic agents, antihistamines, anti-infectives, anti-platelet agents, anti-coagulants, anti-thrombotic agents, anti-scarring agents, anti-proliferative agents, chemotherapeutic agents, anti-neoplastic agents, decongestants, healing promoting agents and vitamins (for example, retinoic acid, vitamin A, depaxapanthenol, vitamin B and their derivatives), hypersomolar agents, immunomodulators, immunosuppressive agents, mucolytics, and combinations and mixtures thereof.

For the treatment of nasal conditions, it may be useful for the drug to comprise an anti-inflammatory agent, an anti-infective agent, an antihistame, a decongestant, a mucolytic agent, or combinations or mixtures thereof. For the treatment of otic conditions, it may be useful for the drug to comprise an anti-inflammatory agent, an anti-infective agent, or combinations or mixtures thereof. For the treatment of throat conditions, it may be useful for the drug to comprise a painkiller, an anti-infective agent, a chemotherapeutic agent, or combinations or mixtures thereof.

In some variations, a mucolytic agent is included in the drug coating to help clear the mucous layer, as previously stated. The mucolytic agent may comprise carbocysteine, erdosteine, acetylcysteine, bromheksin, expigen syrup (sorbimacrogol laurate 300 and ammonium chloride), guaifenesin, glyceryl guaicolate, iodinated glycerol, or combinations or mixtures thereof.

Examples of antioxidants include tocopherol (vitamin E), alpha tocopherol, ascorbic acid, ascorbyl palmitate, butylated hydroxyanisole, butylated hydroxytoluene, citric acid monohydrate, erythorbic acid, ethyl oleate, fumaric acid, malic acid, methionine, monothioglyceraol, phosphoric acid, potassium metabisulfite, proprionic acid, propyl gallate, sodium ascorbate, sodium thiosulfate, sulfur dioxide, citric acid monohydrate, tartaric acid, and thymol.

Examples of local anesthetics include ropivicaine, mepivicaine, cocaine, procaine, lidocaine, hydrocodone, oxycodone and fentanyl, morphine. Examples of vasoconstrictors include epinephrine, levonordefrin, and adrenaline.

Anti-infective agents generally include antibacterial agents, antifungal agents, antiparasitic agents, antiviral agents, antiseptics, iodine (e.g., povidone-iodine), potassium sorbate, sorbic acid, thimersol, thymol, butylene glycol, coconut oil, and vanillin. Anti-inflammatory agents generally include steroidal and nonsteroidal anti-inflammatory agents.

Examples of anti-allergic agents that may suitable for use with the described methods and devices include, but are not limited to, pemirolast potassium (ALAMAST®, Santen, Inc.), and any prodrugs, metabolites, analogs, homologues, congeners, derivatives, salts and combinations thereof. Examples of antiproliferative agents include, but are not limited to, sirolimus, everolimus, temsirolimus, actinomycin D, actinomycin IV, actinomycin I1, actinomycin X1, actinomycin C1, and dactinomycin (COSMEGEN®, Merck & Co., Inc.). Examples of antiplatelet, anticoagulant, antifibrin, and antithrombin agents include, but are not limited to, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibodies, recombinant hirudin, and thrombin inhibitors (ANGIOMAX®, Biogen, Inc.), and any prodrugs, metabolites, analogs, homologues, congeners, derivatives, salts and combinations thereof. Examples of pro-healing agents include, but are not limited to, vitamin A.

Examples of cytostatic or antiproliferative agents that may be suitable for uses with the described methods and devices include, but are not limited to, angiopeptin, angiotensin converting enzyme inhibitors such as captopril (CAPOTEN® and CAPOZIDE®, Bristol-Myers Squibb Co.), cilazapril or lisinopril (PRINIVIL® and PRINZIDE®, Merck & Co., Inc.); calcium channel blockers such as nifedipine; colchicines; fibroblast growth factor (FGF) antagonists, fish oil (omega 3-fatty acid); histamine antagonists; lovastatin (MEVACOR®, Merck & Co., Inc.); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide, and any prodrugs, metabolites, analogs, homologues, congeners, derivatives, salts and combinations thereof.

Examples of antibacterial agents that may be suitable for use with the described methods and devices include, but are not limited to, aminoglycosides, amphenicols, ansamycins, betalactams, f3-lactams such as penicillins, lincosamides, macrolides, nitrofurans, quinolones, sulfonamides, sulfones, tetracyclines, vancomycin, and any of their derivatives, or combinations thereof. Examples of penicillins that may be suitable for use with the described methods and devices include, but are not limited to, amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin G benzathine, penicillin G benzhydrylamine, penicillin G calcium, penicillin G hydrabamine, penicillin G potassium, penicillin G procaine, penicillin N, penicillin O, penicillin V, penicillin V benzathine, penicillin V hydrabamine, penimepicycline, phenethicillin potassium, piperacillin, pivampicillin, propicillin, quinacillin, sulbenicillin, sultamicillin, talampicillin, temocillin, and ticarcillin. In one variation, the antibacterial agent comprises ciprofloxacin. In another variation, the antibacterial agent comprises amoxicillin.

Examples of antifungal agents suitable for use with the described methods and devices include, but are not limited to, allylamines, imidazoles, polyenes, thiocarbamates, triazoles, and any of their derivatives. Antiparasitic agents that may be employed include, but are not limited to, atovaquone, clindamycin, dapsone, iodoquinol, metronidazole, pentamidine, primaquine, pyrimethamine, sulfadiazine, trimethoprim/sulfamethoxazole, trimetrexate, and combinations thereof.

Examples of antiviral agents suitable for use with the described methods and devices include, but are not limited to, acyclovir, famciclovir, valacyclovir, edoxudine, ganciclovir, foscarnet, cidovir (vistide), vitrasert, formivirsen, HPMPA (9-(3-hydroxy-2-phosphonomethoxypropyl)adenine), PMEA (9-(2-phosphonomethoxyethyl)adenine), HPMPG (9-(3-Hydroxy-2-(Phosphonomethoxy)propyl) guanine), PMEG (9-[2-(phosphonomethoxy)ethyl]guanine), HPMPC (1-(2-phosphonomethoxy-3-hydroxypropyl)-cytosine), ribavirin, EICAR (5-ethynyl-1-beta-D-ribofuranosylimidazole-4-carboxamine), pyrazofurin (3-[beta-D-ribofuranosyl]-4-hydroxypyrazole-5-carboxamine), 3-Deazaguanine, GR-92938X (1-beta-D-ribofuranosylpyrazole-3,4-dicarboxamide), LY253963 (1,3,4-thiadiazol-2-yl-cyanamide), RD3-0028 (1,4-dihydro-2,3-Benzodithiin), CL387626 (4,4'-bis[4,6-d][3-aminophenyl-N,N-bis(2-carbamoylethyl)-sulfonilimino]-1,3,5-triazin-2-ylamino-biphenyl-2-,2'-disulfonic acid disodium salt), BABIM (Bis[5-Amidino-2-benzimidazoly-1]-methane), NIH351, and combinations thereof.

Examples of antiseptic agents suitable for use with the described methods and devices include, but are not limited to, alcohol, chlorhexidrine, iodine, triclosan, hexachlorophene, and silver-based agents, for example, silver chloride, silver oxide, and silver nanoparticles.

Anti-inflammatory agents may include steroidal and nonsteroidal anti-inflammatory agents. Examples of suitable steroidal anti-inflammatory agents include, but are not limited to, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, any of their derivatives, and combinations thereof. In some variations, a corticosteroid is used in the sinuses and other bodily structures described herein to prevent or reduce inflammation post-surgery. The corticosteroid will generally be one with high potency, high binding to glucocorticoid receptors, and low bioavailability. For example, in some variations the corticosteroid comprises mometasone furoate, or a pharmaceutically acceptable salt, solvate, hydrate, ester, free base, enantiomer, racemate, polymorph, amorphous, or crystal form thereof. In other variations, the corticosteroid comprises dexamethasone, or a pharmaceutically acceptable salt, solvate, hydrate, ester, free base, enantiomer, racemate, polymorph, amorphous, or crystal form thereof.

Examples of suitable nonsteroidal anti-inflammatory agents include, but are not limited to, COX inhibitors. These COX inhibitors may include COX-1 or COX nonspecific inhibitors such as, for example, salicylic acid and derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone. The COX inhibitors may also include selective COX-2 inhibitors such as, for example, diaryl-substituted furanones such as rofecoxib; diaryl-substituted pyrazoles such as celecoxib; indole acetic acids such as etodolac and sulfonanilides such as nimesulide).

Examples of chemotherapeutic/antineoplastic agents that may be used in the devices described here include, but are not limited to antitumor agents (e.g., cancer chemotherapeutic agents, biological response modifiers, vascularization inhibitors, hormone receptor blockers, cryotherapeutic agents or other agents that destroy or inhibit neoplasia or tumorigenesis) such as alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites or other agents that block cancer cell growth by interfering with certain cell functions, usually DNA synthesis (e.g., 6-mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin), plant (vinca) alkaloids and other anti-tumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase ingibitors such as aminoglutethamide and formestane, trriazole inhibitors such as letrozole and anastrazole, steroidal inhibitors such as exemestane), antiangiogenic proteins, small molecules, gene therapies and/or other agents that inhibit angiogenesis or vascularization of tumors (e.g., meth-1, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, IMC-1C11, IM862, TNP-470, celecoxib (Celebrex), rofecoxib (Vioxx), interferon alpha, interleukin-12 (IL-12) or any of the compounds identified in Science Vol. 289, Pages 1197-1201 (Aug. 17, 2000), which is expressly incorporated herein by reference, biological response modifiers (e.g., interferon, bacillus calmette-guerin (BCG), monoclonal antibodies, interleukin 2, granulocyte colony stimulating factor (GCSF), etc.), PGDF receptor antagonists, herceptin, asparaginase, busulphan, carboplatin, cisplatin, carmustine, cchlorambucil, cytarabine, dacarbazine, etoposide, flucarbazine, flurouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol or paclitaxel, taxotere, azathioprine, docetaxel analogs/ congeners, derivatives of such compounds, and combinations thereof.

Examples of decongestants that may be used in the devices and methods described here include, but are not limited to, epinephrine, pseudoephedrine, oxymetazoline, phenylephrine, tetrahydrozolidine, and xylometazoline. Examples of mucolytics that may be used in the devices and methods described here include, but are not limited to, acetylcysteine, dornase alpha, and guaifenesin. Anti-histamines such as azelastine, diphenhydramine, and loratidine may also be used in the methods and devices described herein.

Suitable hyperosmolar agents that may be used in the devices described here include, but are not limited to, furosemide, sodium chloride gel, and other salt preparations that draw water from tissue or substances that directly or indirectly change the osmolarity of the mucous layer.

Other bioactive agents useful in the present invention include, but are not limited to, free radical scavengers; nitric oxide donors; rapamycin; methyl rapamycin; everolimus; tacrolimus; 40-O-(3-hydroxy)propyl-rapamycin; 40-O-[2-(2-hydroxy)ethoxy]ethyl-rapamycin; tetrazole containing rapamycin analogs such as those described in U.S. Pat. No. 6,329,386; estradiol; clobetasol; idoxifen; tazarotene; alpha-interferon; host cells including, but not limited to prokaryotes and eukaryotes such as, for example, epithelial cells and genetically engineered epithelial cells; dexamethasone; botulinum toxin and other neurotoxins; and, any prodrugs, metabolites, analogs, homologues, congeners, derivatives, salts and combinations thereof.

Examples of free radical scavengers include, but are not limited to, 2,2',6,6'-tetramethyl-1-piperinyloxy, free radical (TEMPO); 4-amino-2,2',6,6'-tetramethyl-1-piperinyloxy, free radical (4-amino-TEMPO); 4-hydroxy-2,2',6,6'-tetramethyl-piperidene-1-oxy, free radical (TEMPOL), 2,2',3,4,5, 5'-hexamethyl-3-imidazolinium-1-yloxy methyl sulfate, free radical; 16-doxyl-stearic acid, free radical; superoxide dismutase mimic (SODm) and any analogs, homologues, congeners, derivatives, salts and combinations thereof. Nitric oxide donors include, but are not limited to, S-nitrosothiols, nitrites, N-oxo-N-nitrosamines, substrates of nitric oxide synthase, diazenium diolates such as spermine diazenium diolate, and any analogs, homologues, congeners, derivatives, salts and combinations thereof.

The selection of drugs, the timing of delivery, and the overall amount of drug or drugs released may be determined by the intended treatment plan, and may be further fine-tuned to meet the specific needs of an individual patient. Components of the drug coating can be altered to adjust the release rates of the drug and/or the transfer rate of the coating to tissue. The drug coating may be formulated so that at least 25%, at least 40%, at least 50%, at least 60% at least 70%, at least 80%, or at least 90% of the coating is transferred to tissue upon expansion of the expandable device. In one variation, at least 80% of the drug coating is transferred. The desired amount of transfer can be accomplished with one or multiple expansions of the expandable device. Furthermore, when multiple expansions are performed with a single device, the drug coating can be formulated to be partially transferred with each expansion. This may be useful when a single device is to be used to treat multiple sites, e.g., multiple sinuses. In some variations, the drug coating can be formulated so that transfer of the drug coating is linear with each expansion, e.g., with each balloon inflation. For example, 25% of the coating can be transferred with the first inflation, another 25% can be transferred with the second inflation, another 25% transferred with the third inflation, and the remaining 25% transferred with the fourth inflation. In other variations, the drug coating can be formulated to have a first order type of transfer where, e.g., 60% of the coating is transferred with the first inflation, 20% of the coating is transferred with the second inflation, 10% is transferred with the third inflation, and 5% is transferred with the fourth inflation. In further variations, the drug coating is provided in multiple layers on the expandable device. In this variation, one layer is transferred with each expansion. Accordingly, the number of layers will generally correspond to the number of expansions intended to be employed. In some cases, a primer coating without drug can be incorporated between each drug layer.

Additionally or alternatively, the surface of the expandable device can be treated prior to coating in a manner that enhances transfer of the drug coating or slows transfer of the drug coating during expansion. For example, when the surface of an inflatable balloon is plasma treated or coated with a primer coating(s), certain parameters of the treatment can be altered to manipulate transfer rates.

The dose of drug delivered (e.g., mometasone furoate) when the drug coating is transferred may range from about 0.5 mg to about 3 mg. For example, the dose of drug transferred may be about 0.5 mg, about 1.0 mg, about 1.5 mg, about 2.0 mg, about 2.5 mg, or about 3.0 mg. In some variations, the dose transferred ranges from about 0.5 mg to about 1.5 mg. In other variations, the dose transferred is more than 3.0 mg. The dose density (i.e., the amount of drug per balloon working length surface area) in the coating (of, e.g., mometasone furoate) may also be adjusted to vary the amount of drug delivered to tissue, and may range from about 100 µg/cm$^2$ to about 600 µg/cm$^2$. For example, the dose density may be 100 µg/cm$^2$, 200 µg/cm$^2$, 300 µg/cm$^2$, 400 µg/cm$^2$, 500 µg/cm$^2$, or 600 µg/cm$^2$.

The coating may include any suitable number or combination of drugs and excipients, depending on the condition to be treated, desired rate of drug release and coating transfer, etc. The coating may include one, two, three, four, or five drugs, or more than five drugs. When two drugs are included in the coating formulation, they can be mometasone furoate and an antihistamine, or mometasone furoate and an antibacterial agent. Likewise, the coating may include one, two, three, four, or five excipients, or more than five excipients. When the tissue to be treated includes mucociliary tissue, it may be beneficial for the drug coating to include one or more penetration enhancing, mucoadhesive, or mucolytic excipients, as previously stated. For example, the drug coating can include mometasone furoate as the drug, polysorbate as the penetration enhancer, polyacrylic acid as the mucoadhesive, and acetylcysteine as the mucolytic. The drug coating may comprise a drug to excipient ratio ranging from about 3:1 to about 1:3.

In one variation, the drug coating formulation comprises a corticosteroid and a mucoadhesive excipient. In another variation, the drug coating formulation comprises a corticosteroid and a mucolytic excipient. In yet a further variation, the drug coating formulation comprises a corticosteroid and a penetration enhancer as the excipient. The drug coating formulation may also include a corticosteroid, a mucoadhesive excipient, and a mucolytic excipient; or a corticosteroid, a mucoadhesive excipient, a mucolytic excipient, and a penetration enhancer. The corticosteroid in the aforementioned drug coatings can be mometasone furoate. Other drug coating formulations may include an antibacterial agent in combination with one or more of a mucoadhesive excipient, a mucolytic excipient, and a penetration enhancer. In some instances, the mucolytic may be the active drug instead of the excipient in the drug coating.

The drug coating formulation may comprise mometasone furoate as the active agent, and as excipients, poly(vinyl pyrrolidone) and polysorbate 80. This drug coating variation may be useful in treating a nasal condition, e.g., rhinitis, sinusitis, or mucosal inflammation. Other drug coatings for treating nasal conditions may include mometasone furoate, poly(vinyl pyrrolidone), polysorbate 80, and poly(ethylene glycol). Alternatively, the drug coatings for treating a nasal condition may include mometasone furoate as the active agent, and as excipients, poly(ethylene glycol) and polysorbate 80. In further variations, the drug coatings for treating a nasal condition may include mometasone furoate as the active agent, and as excipients, poly(vinyl pyrrolidone) and propylene glycol. Other excipient combinations that may be included with mometasone furoate as the active agent are: poly(vinyl pyrrolidone) and polysorbate 80; poly(ethylene glycol) and propylene glycol; and poly(ethylene glycol) and glycerol caproate. In some variations, the coating for treating a nasal condition comprises an antibacterial as the active agent, e.g., amoxicillin, and polysorbate 80 as the excipient. In other variations, the coating for treating a nasal condition comprises an antibacterial as the active agent, e.g., amoxicillin, and poly(vinyl pyrrolidone) as the excipient. In yet further variations, the coating for treating a nasal condition comprises an antibacterial as the active agent, e.g., amoxicillin, and poly(ethylene glycol) as the excipient. Alternatively, the coating for treating nasal conditions may include an antibacterial as the active agent, e.g., amoxicillin, and a combination of polysorbate 80, poly(vinyl pyrrolidone), and poly(ethylene glycol) as excipients. When the nasal condition involves treating the inferior turbinate, the drug coating may be layered onto a non-compliant spherical balloon having a diameter of, e.g., 15 mm to about 50 mm, and the balloon inflated for a time period of about 5 seconds. When the nasal condition involves treating one or more the sinus ostia, the drug coating may be placed on a cylindrical balloon (either compliant, non-compliant, or semi-compliant) having a diameter of, e.g., about 4 mm to about 6 mm, and a length of about 10 mm to about 25 mm. Here the balloon may also be inflated for a time period of about 5 seconds to about 5 minutes. A single balloon can be inflated multiple times at the same of different target tissue site (e.g., the inferior turbinate or one or more sinus ostia), as previously stated.

When an otic condition is to be treated, the drug coating formulation may include an antibacterial agent, an anti-inflammatory agent, e.g., a corticosteroid such as dexamethasone, or combinations thereof, in addition to an excipient or combination of excipients. For example, the antibacterial agent may comprise ciprofloxacin or amoxicillin, and the excipient may comprise a polysorbate, poly(vinyl pyrrolidone), or poly(ethylene glycol). In one variation, the drug coating formulation comprises ciprofloxacin as the antibacterial, and polysorbate 80 as the excipient. In another variation, the drug coating formulation comprises ciprofloxacin as the antibacterial, and poly(vinyl pyrrolidone) as the excipient. In yet further variations, the drug coating formulation comprises ciprofloxacin as the antibacterial agent, and poly(ethylene glycol) as the excipient. In some instances, it may useful for the drug coating formulation to include ciprofloxacin and polysorbate 80, poly(vinyl pryrrolidone), and poly(ethylene glycol) as excipients. When the otic condition involves treating the external ear or Eustachian tube, the drug coating may be layered onto a cylindrical compliant balloon having dimensions of, e.g., 3 mm diameter×20 mm length. Here the balloon may be inflated for a time period of about 5 seconds to about 5 minutes. In some instances, a coated non-compliant or semi-compliant balloon may be useful in treating otic conditions.

When a throat condition is to be treated, the drug coating formulation may include as the active agent, a painkiller, an anesthetic, an anti-inflammatory agent, e.g., a corticosteroid, and combinations thereof. Here the drug coating may be provided on a compliant, non-compliant, or semi-compliant balloon depending on the specific throat condition being treated, and the balloon inflated for about 5 seconds to about 5 minutes. For example, if the balloon is to be used to treat esophageal stenosis, a compliant balloon may be selected and inflated multiple times for about 5 seconds. Other exemplary drug coating formulations are provided below in Table 1. It is understood that the combinations listed above or in Table 1 are not exclusive or limiting, and that any suitable drug(s) and excipient(s) for the desired indication may be used in the coating formulations.

TABLE 1

| Formulation | Drug (D) | Excipient(s) (E) | D:E Ratio |
|---|---|---|---|
| 1 | MF* | Polysorbate | 1:1 |
| 2 | MF* | Polysorbate | 1:1.3 |
| 3 | MF* | Polysorbate | 1:2 |
| 4 | MF* | Poly(ethylene glycol) | 1:1.3 |
| 5 | MF* | Poly(ethylene glycol) | 1:2 |
| 6 | MF* | Poly(ethylene glycol):Polysorbate | 1:1:0.05 |
| 7 | MF* | Poly(ethylene glycol):Polysorbate | 1:2:0.05 |
| 8 | MF* | Poly(vinyl pyrrolidone):propylene glycol | 1:1:0.2 |
| 9 | MF* | Poly(vinyl pyrrolidone):propylene glycol | 1:2:0.2 |
| 10 | MF* | Poly(vinyl pyrrolidone):polysorbate | 1:1:0.03 |
| 11 | MF* | Poly(vinyl pyrrolidone):polysorbate | 1:2:0.03 |
| 12 | MF* | Poly(ethylene glycol):Propylene glycol | 1:1:01 |

TABLE 1-continued

| Formulation | Drug (D) | Excipient(s) (E) | D:E Ratio |
|---|---|---|---|
| 13 | MF* | Poly(ethylene glycol):glycerol caproate | 1:1:01 |
| 14 | MF* | Poly(ethylene glycol):glycerol caproate | 1:2:0.1 |

*Mometasone Furoate

Delivery Device

The expandable devices described here may be delivered using any suitable delivery device. The delivery device may be configured to deliver the expandable device and may be used to move the expandable device into an expanded configuration. The expandable device may be loaded into the delivery device in the low-profile configuration, deployed from the delivery device at the treatment site, and then expanded (e.g., inflated, in instances when the expandable device is an inflatable structure) to the expanded configuration. Deploying the expandable device may comprise distally advancing the expandable device beyond the distal end of the delivery device. Alternatively, deploying the expandable device may comprise maintaining the expandable device at the desired location while proximally retracting the delivery device. Various ports, e.g., for irrigation and/or advancing viewing or imaging elements may also be included in the delivery device.

In some variations, the delivery device may comprise a short stiff catheter, for example, where a therapeutic treatment is being performed in the nasal passageways or sinus cavities where the distance from the point of insertion to the treatment site is relatively short. Other delivery devices may include a malleable tip, e.g., with a bending angle range of up to about 135 degrees, to aid in optimizing access to the frontal, sphenoid, or maxillary sinuses. In some other variations, the delivery device may comprise a small guiding catheter. For example, in variations in which the expandable device is delivered to the Eustachian tube, the delivery device may be configured to navigate to the cartilaginous part of the tube and may comprise a small guiding catheter that is sized and configured to avoid the bony part of the tube and the location of several critical arteries so as not to disrupt them. In further variations, the expandable device is delivered to the target tissue site over a guidewire.

In some variations, the systems described here may comprise a sheath configured to cover the expandable device. The sheath may be used as an alternative to or in addition to a delivery catheter. The catheter and/or sheath may protect the drug coating from scraping off before or during delivery, keep the drug coating dry until deployment, and/or maintain the expandable member in the low-profile configuration. The sheath may be used with a non-compliant expandable device to return the device to a low-profile configuration, such that pleating or refolding of the non-compliant expandable device is not necessary post coating. Instead of a sheath, a topcoat could be layered onto the drug coating to protect it until deployment, as previously stated.

In some variations, the sheath may be elastic and may be expanded to be installed on and around the expandable device without moving or disrupting the drug coating, as described below. The sheath may be scored, perforated or otherwise configured to be removed from the expandable member once the expandable member is at the treatment site.

After the expandable device is inflated and the drug is transferred from the expandable device to the tissue, in some variations, the delivery device may also be used to remove the expandable device from the treatment site. In some variations, the inflation fluid may be removed from the expandable member in order to deflate the expandable member to a low-profile configuration. The delivery device may receive the deflated expandable member for removal by distally advancing the catheter over the expandable member, or proximally retracting the expandable member.

Methods

The expandable devices described here may be delivered to any suitable portion of the anatomy in any suitable manner. As mentioned above, the expandable devices may be used for the treatment of certain conditions or diseases of the nose, ear, and throat, wherein it is desirable to maintain a therapeutic level of a locally delivered drug for a desired period of time. As previously described, in some variations, the expandable device may be delivered to a sinus cavity, sinus ostium, paranasal sinus, ethmoid sinus, inferior turbinate, middle turbinate, osteomeatal complex, and/or nasal cavity. The method may be for treating nasal conditions such as post-surgical inflammation, rhinosinusitis, and/or allergic rhinitis, for example. In other variations, the expandable device may be delivered to the Eustachian tube, external ear canal, and/or inner ear. The method may be for treating otic conditions such as post-surgical inflammation, otitis media, Meniere's disease, and/or tinnitus. In yet other variations, the expandable device may be delivered to the throat for the treatment of post-surgical pain, such as tonsillectomy pain, or for oncology (e.g., esophageal cancer), airway stenosis, chronic laryngitis, or epiglottitis.

Generally, the expandable devices may be delivered in a minimally invasive fashion. In these instances, the expandable devices may be delivered in a low-profile configuration. The expandable devices may be preloaded in or on a delivery device, but need not be. Generally, at least a portion of the delivery device may be introduced into the body. In some variations, the delivery device may be introduced into a natural opening in the body, such as a nostril. In other variations, the delivery device may be introduced into an opening formed in the body via one or more procedures (e.g., a surgically-formed opening). In some of these variations, the artificially-created opening may be pre-formed using one or more tools that are separate from the delivery device. In some variations, one or more portions of the delivery device may be used to create the opening. In other variations, one or more portions of the expandable device may be used to create the opening.

Once the delivery device is introduced into the body, at least a portion of the delivery device may then be advanced to a target location. In some variations, this advancement may occur under direct visualization. The direct visualization may be achieved by a device external to the delivery device, such as an endoscope, or it may be achieved by one or more visualization devices separate from the delivery device, or it may be achieved by one or more visualization devices attached to the delivery device or disposed within one or more portions (i.e., a lumen of a cannula) of the delivery device. In some variations, electromagnetic localizer elements may be included on the expandable device or delivery device to enable navigation by an electromagnetic tracking technology. Additionally or alternatively, the advancement may occur under indirect visualization, such as fluoroscopy, ultrasound, or computer image guidance. In other variations, the delivery device may include an optical fiber that illuminates the position of the device with respect to the target tissue or area to be treated (e.g., a sinus). The illumination may be visible from outside the patient. In further variations, such as in some instances of delivery to the middle turbinate, the expandable device may be delivered without direct or indirect visualization.

After the expandable device is delivered to the target location, the expandable device may be expanded into an expanded configuration. In variations where the expandable device is expandable in response to one or more forces or stimuli, one or more appropriate forces of stimuli may be applied to the expandable device to expand the expandable device into an expanded configuration. For example, when the expandable device is an inflatable structure (e.g., a balloon), the inflatable structure may be expanded into an expanded configuration by delivery of a liquid or gas to the interior of the inflatable structure. In variations in which the expandable device is compliant, the expandable device may distend with inflation to the expanded configuration. In other variations, e.g., when the expandable device is pleated, folded, or wrapped to assume a low-profile configuration, upon inflation, the expandable device may unfurl to expand to the expanded configuration. In yet other variations, the expandable device may both distend with inflation and unfurl with inflation, for example, when the expandable device is semi-compliant. The expanded device in its expanded configuration may be shaped as shown in FIGS. 1A-1L. It is understood that other shapes may be employed that are tailored to the specific anatomy to be treated.

The expandable device may be expanded one or multiple times to transfer the drug coating, dilation of tissues, or both. Once expanded, the expandable device may be configured to conform at least partly to the shape of the bodily structure and substantially contact the bodily structure. For example, the expandable device may conform to the sinus or nasal cavity and substantially contact the sinus or nasal cavity wall. The percentage of surface area of the expandable device in contact with the cavity wall may be sufficient to transfer the drug coating and provide the appropriate delivery of one or more drugs to the tissue. For example, about 10% to about 100%, about 20% to about 100%, about 30% to about 100%, about 40% to about 100%, about 50% to about 100%, about 60% to about 100%, about 70% to about 100%, about 80% to about 100%, or about 90% to about 100% of the surface area of the expandable device may be in contact with the sinus or nasal cavity wall. In some instances, the expansion of the expandable device may act to anchor the expandable device against or into tissue. In other instances, it may be useful to control the direction of expansion to target a particular area for treatment. Directional expansion may be achieved using a directional balloon (e.g., as shown in FIGS. 1F and 1L), or by including as part of the delivery system, a rotatable sheath with an opening or cut-out that is capable of exposing only the intended surface area of the expandable device for targeted expansion and tissue contact, or for directionally anchoring the expandable device against the tissue for increased contact.

As mentioned above, the pressure of the expandable device when expanded may be sufficient for maintaining contact of the surface against the sinus or nasal mucosa, or other bodily structure described herein, but not cause unwanted damage or reshaping. For example, when the expandable device is a compliant balloon, the inflation pressure of the compliant balloon may be between about 2 atm and 16 atm, more specifically between about 4 atm and 6 atm.

The expandable device may be left in place for any suitable amount of time. It may be desirable for the expandable device to be left in place for a sufficient period to transfer the drug coating and deliver one or more drugs to the tissue. As previously described, the drug coating may be formulated with a high drug-to-excipient ratio to enhance fast release from the expandable device during a short time period of inflation. Expansion times (e.g., inflation times) ranging from under one minute to multiple hours may be utilized for ear and nasal applications for enhanced drug uptake. For example, in some variations the expandable device may be left in place (expanded) for about 5 seconds to about 2 hours, about 30 seconds to about 2 hours, about 5 minutes to about 1 hour, about 30 seconds to 5 minutes, about 5 seconds to about 5 minutes, or about 10 minutes to about 30 minutes. In some variations, the expandable device and/or drug coating is structured so that a physician can control the amount of coating (and thus, drug) delivered by controlling the expansion time (e.g., inflation time). In other words, the amount of drug delivered can be based on the duration of expansion at the one or multiple tissue sites, e.g., one or more paranasal sinuses. In another variation, the expandable device is left in place for about 5 seconds. A shorter expansion time may result in overall less mucosal injury and thus may be beneficial when drug delivery to multiple sinuses or target sites is to be performed. In some variations, the entire procedure may be performed during a single doctor office visit. In other variations, where the expandable device is to be left expanded and in place for longer periods of time (e.g., 1-2 hours), the expandable device may comprise a pressure valve that the patient may release him/herself outside of the doctor's office.

In further variations, multiple expansion-collapse cycles (e.g., inflation-deflation cycles) of the same expandable device could be used to release multiple coating layers to a single or multiple tissue sites. Each inflation-deflation cycle could be of the same or different duration. A single expandable device may also be repeatedly expanded to treat multiple/different sinuses. For example, a single expandable device may be used to treat two to eight sinuses. Specifically a single expandable device may be used to treat two sinuses, three sinuses, four sinuses, five sinuses, six sinuses, seven sinuses, or eight sinuses. In one variation, a single expandable device may be used to treat two frontal sinuses and two maxillary sinuses and/or two sphenoid sinuses. In other variations, multiple expansions can be used to transfer drug across inferior and middle turbinates.

Upon transference of the drug coating from the expandable device to the tissue, the delivery device and expandable device may be removed. Prior to removal, the expandable device may be collapsed or otherwise returned to a low-profile configuration. As described above, in variations in which the expandable device comprises an inflatable device, the inflation fluid may be withdrawn from the expandable device and the expandable device deflated to the low-profile configuration. When multiple inflations are to be performed, the inflatable device may be configured to rapidly deflate or collapse back to its pleated/folded state to prevent loss of the remaining drug. The delivery device may then be used to receive the expandable device and the expandable device and delivery device removed from the body, or the expandable device may be removed without the use of the delivery device, or using a separate device.

After the drug and/or coating are transferred to the tissue, it may be eluted gradually over time. For example, the formulation may be configured for sustained release of drug at a therapeutic level for a period of days, weeks, or months. In some variations, a therapeutic level of drug delivery may be provided for up to 5 days, up to 14 days, up to 30 days, up to 45 days, up to 60 days, up to 75 days, or up to 90 days, depending on the specific treatment application. In other variations, the treatment time may range from about 2 months to about 3 months. For example, when the method is intended for treatment of allergic rhinitis applications, it may be desirable to maintain a therapeutic level of drug for the duration of an allergy season (e.g., about 2 months to about 3 months). When a drug is to be delivered after functional endoscopic sinus surgery (FESS), the formulation may be configured to release the drug over a period of about 14 to 28 days. When a drug is to be delivered after balloon sinuplasty alone, the formulation may be configured to release the drug over a period of about 7 to 14 days.

In some instances, the method of treatment may comprise multiple rounds of treatment. For example, patients who suffer from chronic conditions, such as otitis media, or who experience more than one allergy season (e.g., due to different allergens) each year, may get multiple treatments during the year. This may provide continuous therapeutic treatment in healing the condition and/or sustained relief from the symptoms associated with the condition.

For applications where long-term mechanical support is desirable, the methods described herein may be combined with an implantable device. For example, the methods described herein may be combined with the placement of a scaffold or stent. In some variations, the scaffold or stent may be drug eluting. In some variations the scaffold or stent may be expandable (e.g., balloon expandable or self-expanding). In some variations, the scaffold or stent may be bioresorbable (e.g., comprise a bioresorbable synthetic biopolymer), but need not be.

When the methods described herein are combined with an implantable device, the expandable devices described herein may be used to deliver a drug before implantation of the implant, or may be used post-implantation of the implant. In variations in which the expandable device is used first, the device may help pre-dilate the ostia for improved ease of delivery and implantation of the implant. In variations in which the expandable device is used second, the device may help post-dilate the implant for improved apposition. In addition to helping deliver an effective localized dose of a drug, when combined with a scaffold or stent, the methods described here may, for example, maintain the patency of the sinus cavities, and help prevent obstruction caused by adhesions between healing or inflamed mucosal surfaces.

Manufacturing

The devices described herein may be made in any suitable manner. In general, molds may be used to form expandable devices designed for specific anatomies, and the materials selected for the expandable device may be based on desired compliance for the specific application.

Drugs may be coated on the expandable member when fully inflated, partially inflated, or folded. Coating an inflated expandable device may maximize drug delivery and tissue coverage. In some variations where the expandable device is folded, the drugs may be coated on the certain regions of the expandable device that become protected upon folding of the expandable device. This may help to protect the coating during delivery or loading into a delivery device or sheath. Pleat geometry such as pleat number, length, and shape can be adjusted for the desired amount of drug coverage during refold. Tight refolding to a low profile may be beneficial in keeping drug loss during delivery but prior to inflation at less than about 10%. This selective coating may be achieved by masking of the region that is desired to be non-coated. In other variations, drugs may be coated on a portion of the expandable device based on a desired treatment area within the target cavity. For example, an expandable device intended for use in the nasal cavity may be coated on one side to deliver drug to the turbinates, but uncoated on a second side to minimize drug delivery to the nasal septa (e.g., to prevent any deterioration of the septa). An expandable device to be used at multiple treatment sites and/or expanded multiple times may be provided with a multi-layered coating.

In some variations, the drug coating may be patterned on the expandable device or provided on specific areas of the expandable device, depending on, e.g., the anatomy or particular target tissue site to be treated. For example, the pattern could include solid or dashed lines of the drug coating, the drug coating dotted on the expandable device, or the drug coating provided as a spiral around the expandable device, etc. The thickness of the drug coating may range from about 10 µm to about 500 µm. In some variations, the thickness of the drug coating can be varied, e.g., structured to be thicker on some areas of the expandable device than others.

Drug coating may be achieved by methods such as spray coating, pipette or syringe coating, or dip coating. Spray coating may achieve improved tissue uptake and drug delivery uniformity. Spray coating may provide homogenous distribution of the drug in the coating. For improved coating adhesion, the expandable device may be cleaned with a solvent and dried prior to coating. In addition, plasma treatment with an inert gas, such as argon or oxygen, after cleaning may increase the cleaning and wettability of the expandable device surface leading to increased coating adhesion and release of the coating upon contact with mucus at the mucosal tissue site. One or more parameters of the plasma treatment can be altered to adjust drug release to the desired rate. For example, power, flow rate of the inert gas, cycle time, and number of cycles can be manipulated to adjust the rate of drug release. Table 2 provides a list of exemplary parameters for plasma treatment. In some variations, the expandable device may be primed with a hydrophilic excipient to enhance drug release. In other variations, the expandable device may be primed with a hydrophobic (lipophilic) excipient to slow drug release. The hydrophilic to lipophilic properties of the excipient are selected for either a faster or slower release rate. The priming can be performed alone or in addition to cleaning and plasma treatment.

TABLE 2

Exemplary Parameters for Plasma Treatment

| RF Power (watts) | Oxygen Flow Rate (cc/min) | Argon Flow Rate (cc/min) | Plasma Time/ Cycle (min) | # of Cycles |
| --- | --- | --- | --- | --- |
| 100 | 0 | 40 | 5 | 3 |
| 100 | 20 | 20 | 10 | 2 |
| 100 | 40 | 0 | 15 | 1 |
| 100 | 10 | 30 | 10 | 3 |
| 125 | 15 | 25 | 7 | 2 |
| 150 | 20 | 20 | 5 | 1 |

TABLE 2-continued

Exemplary Parameters for Plasma Treatment

| RF Power (watts) | Oxygen Flow Rate (cc/min) | Argon Flow Rate (cc/min) | Plasma Time/ Cycle (min) | # of Cycles |
|---|---|---|---|---|
| 175 | 25 | 15 | 3 | 3 |
| 200 | 30 | 10 | 1 | 2 |
| 300 | 15 | 0 | 1 | 1 |
| 100 | 0 | 15 | 20 | 1 |

After coating of the expandable device, e.g., a balloon, the expandable device may be re-folded at an elevated temperature, e.g., at about 50 degrees Celsius, about 60 degrees Celsius, about 70 degrees Celsius, or about 80 degrees Celsius, and for about 5 minutes, about 30 minutes, or about one hour, to achieve a low profile. In some variations, the balloon may be re-folded under vacuum at a reduced pressure and temperature while applying vacuum to its interior volume to obtain a low profile. Re-folding of the expandable device can be followed by sheathing, packaging in a foil pouch with argon, nitrogen or other inert gas, and sterilization using gamma irradiation or electron beams.

In some variations, the manufacturing method may include cleaning the balloon surface and/or treating the balloon with plasma, inflating the balloon, spray coating the balloon with a drug coating formulation, drying the balloon coating at room temperature or elevated temperature, and re-folding the balloon as described above.

Figure 2:
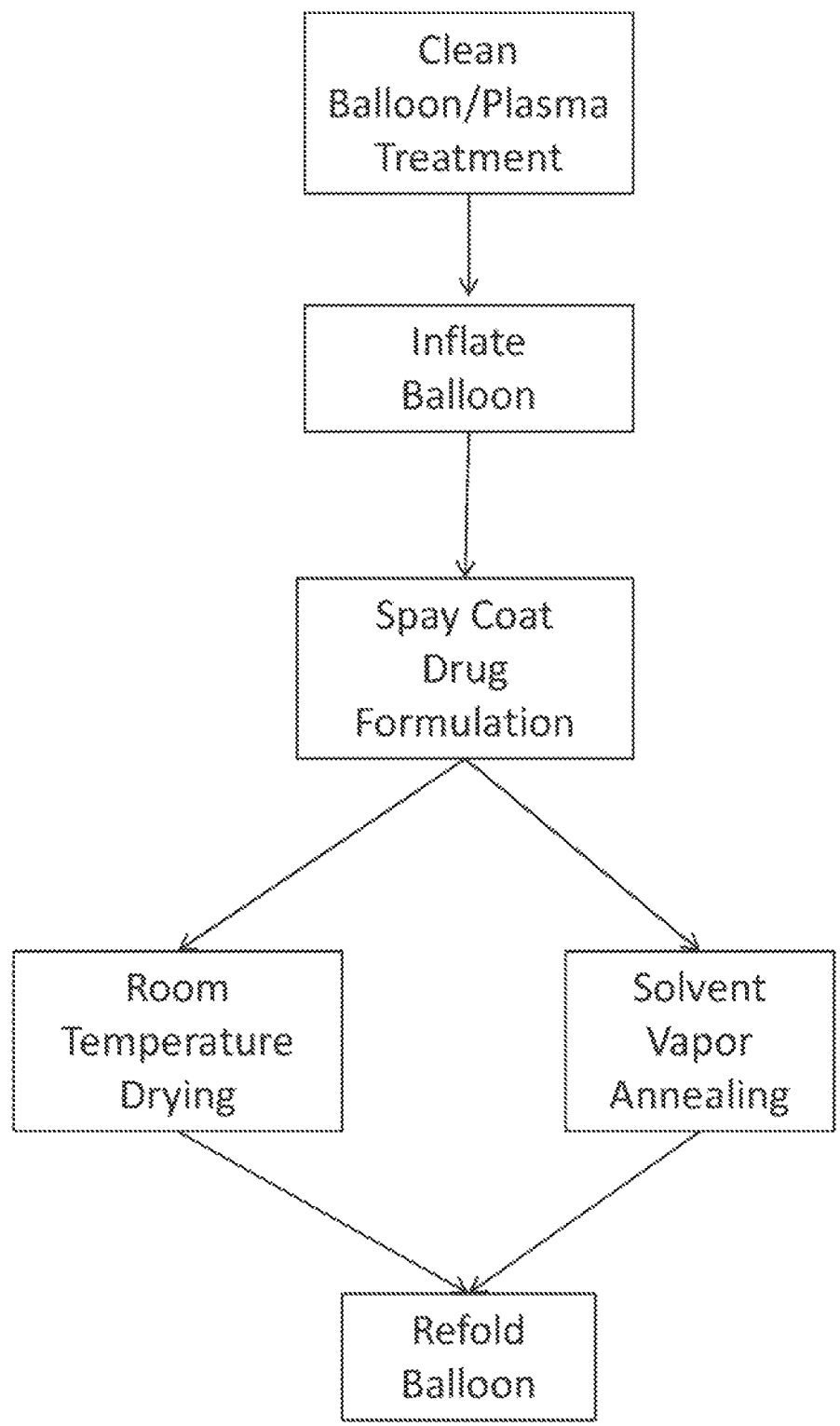
FIG. 2 illustrates exemplary processes for coating the expandable device.

In other variations, the manufacturing method may include cleaning the balloon surface and/or treating the balloon with plasma, inflating the balloon, spray coating the balloon with a drug coating formulation, exposing the coated balloon to a solvent vapor (solvent vapor annealing), and re-folding the balloon as described above. These manufacturing processes are outlined in FIG. 2. Suitable solvent vapors may include, but are not limited to, water, acetone, methanol, ethanol, 2-propanol, 1-propanol, linear alcohols, methane, ethane, propane, butane, pentane hexane, cyclohexane, heptane, methyl iso-butyl ketone, methyl ethyl ketone, dimethylsulfoxide, dimethylacetamide, dimethylformamide, formamide, methyl acetate, ethyl acetate, propyl acetate, isopropyl acetate, n-butyl acetate, dimethyl ether, diethyl ether, dipropyl ether, N-methylpyrrolidone, dichloromethane, chloroform, difluoromethane, fluoroform, freons, benzene, toluene, xylene, blends thereof, and combinations thereof. The preferred vapor can depend on a number of variables such as the compositions of the coatings and surfaces of the expandable device. In further variations, the manufacturing method includes drying the balloon coating at room temperature and exposing the coated balloon to a solvent vapor.

The drying conditions and/or exposure to solvent vapor may affect drug morphology in the coating. For example, the particular solvent vapor used, duration of solvent vapor exposure, and/or drying rate (e.g., slower drying) during coating and post-coating may be used to control the crystallinity of the drug. The ability to control drug morphology may be useful since crystalline drug forms typically exhibit greater residence times in tissue, and may be beneficial when a longer period of drug delivery is desired. In variations where shorter periods of drug delivery are needed, faster drying, shorter exposure to solvent vapor, or a particular solvent vapor may be used to provide more amorphous drug in the coating. Thus, in some instances the manufacturing methods can be tailored to provide a coating that includes a crystalline form of the drug. In other instances, the manufacturing methods can be tailored to provide a coating that includes the amorphous form of a drug. In yet further instances, the manufacturing methods can be tailored to provide a coating having a mixture of crystalline and amorphous forms of a drug. For example, the manufacturing methods can be manipulated to provide a coating including about 100% amorphous drug, about 5% to about 10% of crystalline drug (and about 90% to about 95% amorphous drug), about 20% to about 25% crystalline drug (and about 75% to about 80% amorphous drug), about 50% crystalline drug (and about 50% amorphous drug), or greater than about 50% crystalline drug (less than 50% amorphous drug). For the treatment of nasal or mucosal conditions, it may be useful for the coating to provide mometasone furoate in crystalline or amorphous forms, or a combination of crystalline and amorphous forms. In some variations, about 25% to about 75% of the mometasone furoate is provided in crystalline form in the drug coating.

In addition to the particular components of the coating formulation, the manufacturing methods described herein may help minimize drug loss during delivery to the treatment site and maximize drug delivery upon inflation and contact with tissue.

EXAMPLES

Example 1: Manufacture of an Expandable Device with an Air Dried Drug Coating A 30 mm compliant 80A Pellethane® balloon was cleaned with 70% isopropanol and air dried. The balloon was then treated with oxygen plasma and later spray coated with a mometasone furoate formulation listed in Table 1. The coating was allowed to dry at room temperature overnight. Post-spray pass drying was completed using nitrogen gas. The balloon was then re-folded and heat set using a custom pleating machine. The coated balloon was sheathed and packaged under nitrogen gas and sterilized by electron beam irradiation.

Example 2: Drug Loss and Release from Air Dried Drug Coating in an Ovine Model A drug coated balloon made using the process described in Example 1 was advanced through a sheep nostril using a rigid 4 mm endoscope to the inferior turbinate, expanded for 5 minutes, and then deflated and removed from the nostril. Follow-up studies found that less than 10% drug loss occurred prior to inflation. The drug coating remaining on the non-inflated balloon tracked to the nasal passage and removed was dissolved in acetonitrile and the amount of drug quantified by HLPC. In this study, more than about 80% of drug was released after 5 minutes of inflation.

Example 3: Manufacture of an Expandable Device with a Drug Coating Exposed to Solvent Vapor A 30 mm 80A Pellethane® compliant balloon was cleaned with 70% isopropanol and dried in an oven. The balloon was then treated with oxygen plasma and immediately spray coated with a mometasone furoate formulation listed in Table 1. Post-spray pass drying was conducted with nitrogen gas. Next, the drug coated balloon was treated by solvent vapor annealing (i.e., exposed to a solvent vapor) in a sealed chamber saturated with ethanol for four hours at room temperature. After solvent vapor annealing, the balloon was re-folded and heat set using a custom pleating machine. The coated balloon was then sheathed and packaged under nitrogen gas and sterilized by electron beam irradiation.

Figure 3:
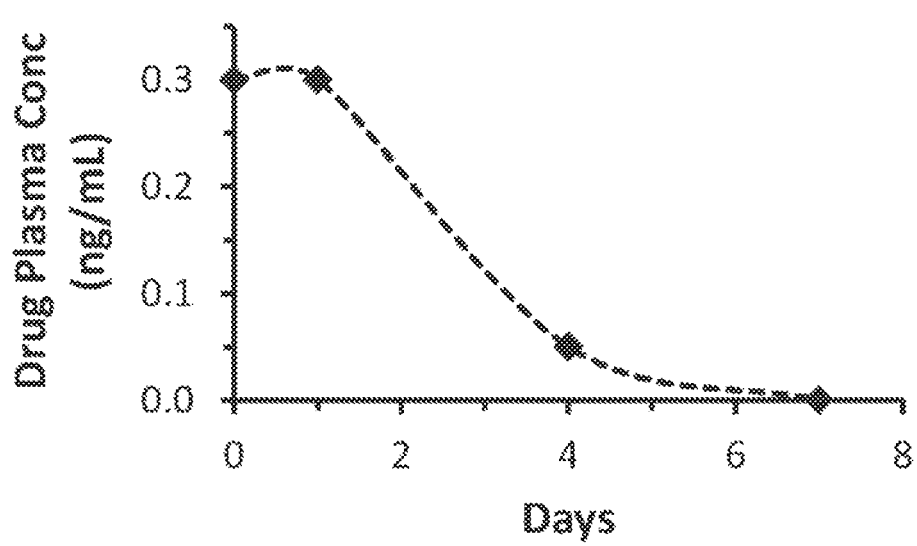
FIG. 3 is a graph that illustrates the blood plasma concentration of mometasone furoate after delivery of a drug coating to an ovine maxillary sinus over a 7 day period.

Example 4: Drug Uptake and Plasma Concentration of Drug Coating Exposed to Solvent Vapor in an Ovine Model A drug coated balloon made using the process described in Example 3 was advanced to a sheep maxillary sinus using a rigid 4 mm endoscope and expanded for 5 minutes, and then deflated and removed from the nostril. After 7 days the animal was sacrificed and tissue samples obtained from the maxillary sinus and surrounding tissues. HPLC studies conducted on the tissue samples found that the maxillary sinus tissue had a mometasone furoate concentration of 146 ng/g (nanograms of drug per gram of tissue), and that tissues surrounding the maxillary sinus had a mometasone furoate concentration of 55 ng/g, proving that an efficacious level of drug was achieved. Plasma concentration of mometasone furoate was also measured over 7 days. Referring to Table 3 below and FIG. 3, mometasone furoate (MF) plasma concentration was low and found to decrease over the 7 day period from an initially low value. This study demonstrated that high local tissue (sinus tissue) concentrations of drug can be achieved with the drug coated balloons while minimizing the risk of systemic exposure. Low systemic exposure generally lowers the risk of a patient experiencing side effects from the delivered drug.

TABLE 3

| Days | MF Plasma Concentration (ng/mL) |
|---|---|
| 0 | 0.3 |
| 1 | 0.3 |
| 4 | 0.05 |
| 7 | <0.01 |

Example 5: Increasing Drug Crystallinity Using Solvent Vapor Annealing

A 30 mm 10A ChronoPrene® compliant balloon was cleaned with 70% isopropanol and air dried. The balloon was then treated with oxygen plasma and immediately spray coated with a mometasone furoate formulation listed in Table 1. Post-spray pass drying was conducted with nitrogen gas. Next, the drug coated balloon was treated by solvent vapor annealing (i.e., exposed to a solvent vapor) in a sealed chamber saturated with ethanol for two hours at room temperature. Microscopic examination of the drug coating before and after solvent vapor annealing found increased crystallinity of the mometasone furoate after exposure to the ethanol vapor. The coated balloon were then sheathed and packaged under nitrogen gas and sterilized by electron beam irradiation.

Although the foregoing invention has, for the purposes of clarity and understanding been described in some detail by way of illustration and example, it will be apparent that certain changes and modifications may be practiced, and are intended to fall within the scope of the appended claims.

The invention claimed is:

1. An expandable device configured for delivering a therapeutic agent to a nasal, otic, or throat tissue site, comprising:
   a drug coating on an external surface of the expandable device; and
   an internal volume configured to receive a fluid,
   wherein the expandable device has a low-profile configuration and an expanded configuration, and
   wherein the drug coating comprises a mixture of crystalline and amorphous forms of a drug, the drug in the drug coating having a dose density ranging from about 100 µg/cm$^2$ to about 600 µg/cm$^2$.

2. The device of claim 1, wherein the drug coating is applied to the external surface of the expandable device by a process, comprising:
   providing the expandable device having a low-profile configuration and an expanded configuration;
   treating the expandable device by a plasma process;
   spray coating the expandable device in the expanded configuration with a drug; exposing the expandable device to a solvent vapor; and
   folding the expandable device into the low-profile configuration.

3. The device of claim 2, wherein the drug coating is applied to the external surface of the expandable device by a process further comprising priming the expandable device with a hydrophilic excipient, a hydrophobic excipient, an amphiphilic excipient, a lipophilic excipient, or a combination thereof.

4. The device of claim 1, wherein the mixture of crystalline and amorphous forms of the drug is at a ratio of about 5%-10% crystalline drug to about 95%-90% amorphous drug.

5. The device of claim 1, wherein the mixture of crystalline and amorphous forms of the drug is at a ratio of about 20%-25% crystalline drug to about 80%-75% amorphous drug.

6. The device of claim 1, wherein the mixture of crystalline and amorphous forms of the drug is at a ratio of about 50% or greater crystalline drug to about 50% or less amorphous drug.

7. The device of claim 1, wherein the drug coating comprises mometasone furoate or pharmaceutically acceptable salts, solvates, hydrates, esters, free base, enantiomers, racemates, polymorphs, amorphous, or crystal forms thereof.

8. The device of claim 7, wherein about 25% to about 75% of the mometasone furoate is in crystalline form.

9. The device of claim 1, wherein the drug coating comprises at least one of a local anesthetic, painkiller, vasoconstrictor, antiseptic, antioxidant, anti-inflammatory agent, anti-allergen agent, anti-cholinergic agent, antihistamine, anti-infective agent, anti-platelet agent, anti-coagulant, anti-thrombotic agent, anti-scarring agent, anti-proliferative agent, chemotherapeutic agent, anti-neoplastic agent, decongestant, healing promoting agent, vitamin, hyperosmolar agent, immunomodulator, immunosuppressive agent, penetration enhancer, mucoadhesive, mucolytic, or combination thereof.

10. A method for treating a nasal, otic, or throat tissue site, comprising:
    providing an expandable device having a low-profile configuration, an expanded configuration, and an external surface, the external surface having a drug coating comprising a mixture of crystalline and amorphous forms of a drug, wherein the drug in the drug coating has a dose density ranging from about 100 µg/cm² to about 600 µg/cm²; and expanding the expandable device with a fluid to contact the external surface with the nasal, otic, or throat tissue site.

11. The method of claim 10, wherein the drug coating has been applied to the external surface of the expandable device by:

treating the expandable device by a plasma process;

spray coating the expandable device in the expanded configuration with the drug; exposing the expandable device to a solvent vapor; and folding the expandable device into the low-profile configuration.

12. The method of claim 11, further comprising priming the expandable device with a hydrophilic excipient, a hydrophobic excipient, an amphiphilic excipient, a lipophilic excipient, or a combination thereof.

13. The method of claim 10, wherein the mixture of crystalline and amorphous forms of the drug is at a ratio of about 5%-10% crystalline drug to about 95%-90% amorphous drug.

14. The method of claim 10, wherein the mixture of crystalline and amorphous forms of the drug is at a ratio of about 20%-25% crystalline drug to about 80%-75% amorphous drug.

15. The method of claim 10, wherein the mixture of crystalline and amorphous forms of the drug is at a ratio of about 50% or greater crystalline drug to about 50% or less amorphous drug.

16. The method of claim 10, wherein the drug coating comprises mometasone furoate or pharmaceutically acceptable salts, solvates, hydrates, esters, free base, enantiomers, racemates, polymorphs, amorphous, or crystal forms thereof.

17. The method of claim 16, wherein about 25% to about 75% of the mometasone furoate is in crystalline form.

18. The method of claim 10, wherein the drug coating comprises at least one of a local anesthetic, painkiller, vasoconstrictor, antiseptic, antioxidant, anti-inflammatory agent, anti-allergen agent, anti-cholinergic agent, antihistamine, anti-infective agent, anti-platelet agent, anti-coagulant, anti-thrombotic agent, anti-scarring agent, anti-proliferative agent, chemotherapeutic agent, anti-neoplastic agent, decongestant, healing promoting agent, vitamin, hyperso-molar agent, immunomodulator, immunosuppressive agent, penetration enhancer, mucoadhesive, mucolytic, or combination thereof.

19. An expandable device configured for delivering a therapeutic agent to a nasal, otic, or throat tissue site, comprising:

a drug coating on an external surface of the expandable device; and an internal volume configured to receive a fluid, wherein the expandable device has a low-profile configuration and an expanded configuration; and wherein the drug coating comprises a mixture of crystalline and amorphous forms of a drug at a ratio of about 50% or greater crystalline drug to about 50% or less amorphous drug.

20. The device of claim 19, wherein the drug coating is applied to the external surface of the expandable device by a process, comprising:

providing the expandable device having a low-profile configuration and an expanded configuration;

treating the expandable device by a plasma process;

spray coating the expandable device in the expanded configuration with a drug; exposing the expandable device to a solvent vapor; and folding the expandable device into the low-profile configuration.

21. The device of claim 20, wherein the drug coating is applied to the external surface of the expandable device by a process further comprising priming the expandable device with a hydrophilic excipient, a hydrophobic excipient, an amphiphilic excipient, a lipophilic excipient, or a combination thereof.

22. The device of claim 19, wherein the drug coating comprises mometasone furoate or pharmaceutically acceptable salts, solvates, hydrates, esters, free base, enantiomers, racemates, polymorphs, amorphous, or crystal forms thereof.

23. The device of claim 19, wherein the drug coating comprises at least one of a local anesthetic, painkiller, vasoconstrictor, antiseptic, antioxidant, anti-inflammatory agent, anti-allergen agent, anti-cholinergic agent, antihistamine, anti-infective agent, anti-platelet agent, anti-coagulant, anti-thrombotic agent, anti-scarring agent, anti-proliferative agent, chemotherapeutic agent, anti-neoplastic agent, decongestant, healing promoting agent, vitamin, hyperso-molar agent, immunomodulator, immunosuppressive agent, penetration enhancer, mucoadhesive, mucolytic, or combination thereof.

24. The device of claim 19, wherein the drug in the drug coating has a dose density ranging from about 100 µg/cm² to about 600 µg/cm².

25. A method for treating a nasal, otic, or throat tissue site, comprising:

providing an expandable device having a low-profile configuration, an expanded configuration, and an external surface, the external surface having a drug coating comprising a mixture of crystalline and amorphous forms of a drug, where the mixture of crystalline and amorphous forms of the drug is at a ratio of about 50% or greater crystalline drug to about 50% or less amorphous drug; and expanding the expandable device with a fluid to contact the external surface with the nasal, otic, or throat tissue site.

26. The method of claim 25, wherein the drug coating has been applied to the external surface of the expandable device by:

treating the expandable device by a plasma process;

spray coating the expandable device in the expanded configuration with the drug; exposing the expandable device to a solvent vapor; and folding the expandable device into the low-profile configuration.

27. The method of claim 26, further comprising priming the expandable device with a hydrophilic excipient, a hydrophobic excipient, an amphiphilic excipient, a lipophilic excipient, or a combination thereof.

28. The method of claim 25, wherein the drug coating comprises mometasone furoate or pharmaceutically acceptable salts, solvates, hydrates, esters, free base, enantiomers, racemates, polymorphs, amorphous, or crystal forms thereof.

29. The method of claim 25, wherein the drug coating comprises at least one of a local anesthetic, painkiller, vasoconstrictor, antiseptic, antioxidant, anti-inflammatory agent, anti-allergen agent, anti-cholinergic agent, antihistamine, anti-infective agent, anti-platelet agent, anti-coagulant, anti-thrombotic agent, anti-scarring agent, anti-proliferative agent, chemotherapeutic agent, anti-neoplastic agent, decongestant, healing promoting agent, vitamin, hypersomolar agent, immunomodulator, immunosuppressive agent, penetration enhancer, mucoadhesive, mucolytic, or combination thereof.

30. The method of claim 25, wherein the drug in the drug coating has a dose density ranging from about 100 µg/cm² to about 600 µg/cm².

31. A method for treating a nasal, otic, or throat tissue site, comprising:
providing an expandable device having a low-profile configuration, an expanded configuration, and an external surface, the external surface having a drug coating comprising a mixture of crystalline and amorphous forms of a drug, wherein the drug coating has been applied to the external surface of the expandable device by:
treating the expandable device by a plasma process;
spray coating the expandable device in the expanded configuration with the drug;
exposing the expandable device to a solvent vapor; and
folding the expandable device into the low-profile configuration; and
expanding the expandable device with a fluid to contact the external surface with the nasal, otic, or throat tissue site.

32. The method of claim 31, further comprising priming the expandable device with a hydrophilic excipient, a hydrophobic excipient, an amphiphilic excipient, a lipophilic excipient, or a combination thereof.

33. The method of claim 31, wherein the mixture of crystalline and amorphous forms of the drug is at a ratio of about 5%-10% crystalline drug to about 95%-90% amorphous drug.

34. The method of claim 31, wherein the mixture of crystalline and amorphous forms of the drug is at a ratio of about 20%-25% crystalline drug to about 80%-75% amorphous drug.

35. The method of claim 31, wherein the mixture of crystalline and amorphous forms of the drug is at a ratio of about 50% or greater crystalline drug to about 50% or less amorphous drug.

36. The method of claim 31, wherein the drug coating comprises mometasone furoate or pharmaceutically acceptable salts, solvates, hydrates, esters, free base, enantiomers, racemates, polymorphs, amorphous, or crystal forms thereof.

37. The method of claim 36, wherein about 25% to about 75% of the mometasone furoate is in crystalline form.

38. The method of claim 31, wherein the drug coating comprises at least one of a local anesthetic, painkiller, vasoconstrictor, antiseptic, antioxidant, anti-inflammatory agent, anti-allergen agent, anti-cholinergic agent, antihistamine, anti-infective agent, anti-platelet agent, anti-coagulant, anti-thrombotic agent, anti-scarring agent, anti-proliferative agent, chemotherapeutic agent, anti-neoplastic agent, decongestant, healing promoting agent, vitamin, hypersomolar agent, immunomodulator, immunosuppressive agent, penetration enhancer, mucoadhesive, mucolytic, or combination thereof.

39. The method of claim 31, wherein the drug in the drug coating has a dose density ranging from about 100 µg/cm² to about 600 µg/cm².

* * * * *